US012620455B2

(12) United States Patent　　(10) Patent No.:　US 12,620,455 B2
Roodi et al.　　(45) Date of Patent:　May 5, 2026

(54) MERGING DUPLICATE MARKING TO OPTIMIZE COMPUTER OPERATIONS FOR GENE SEQUENCING PIPELINE

(71) Applicant: Huawei Technologies Co., Ltd., Shenzhen (CN)

(72) Inventors: Meysam Roodi, Richmond Hill (CA); Zahra Lak, Toronto (CA)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 1142 days.

(21) Appl. No.: 17/114,895

(22) Filed: Dec. 8, 2020

(65) Prior Publication Data

US 2021/0174904 A1　Jun. 10, 2021

Related U.S. Application Data

(63) Continuation of application No. PCT/CN2020/078903, filed on Mar. 12, 2020.

(60) Provisional application No. 62/818,519, filed on Mar. 14, 2019.

(51) Int. Cl.
| | |
|---|---|
| *G16B 30/20* | (2019.01) |
| *G06F 16/901* | (2019.01) |
| *G06N 3/126* | (2023.01) |
| *G16B 50/30* | (2019.01) |

(52) U.S. Cl.
CPC ......... *G16B 30/20* (2019.02); *G06F 16/9024* (2019.01); *G06N 3/126* (2013.01); *G16B 50/30* (2019.02)

(58) Field of Classification Search
None
See application file for complete search history.

(56) References Cited

U.S. PATENT DOCUMENTS

| | | | | |
|---|---|---|---|---|
| 9,824,068 B2 * | 11/2017 | Wong | .................... | G16B 30/00 |
| 10,901,887 B2 | 1/2021 | Jacob et al. | | |
| 2012/0330567 A1 | 12/2012 | Bauer et al. | | |
| 2013/0137588 A1 | 5/2013 | Shendure et al. | | |
| 2014/0163900 A1 | 6/2014 | Erlich et al. | | |
| 2014/0280344 A1 | 9/2014 | Draghicescu et al. | | |
| 2014/0288851 A1 | 9/2014 | Park et al. | | |
| 2014/0297196 A1 | 10/2014 | Olson | | |
| 2015/0363549 A1 | 12/2015 | Kimura | | |
| 2017/0337325 A1 | 11/2017 | Olson | | |
| 2018/0121601 A1 * | 5/2018 | Hahm | .................... | G16B 50/40 |
| 2019/0385703 A1 | 12/2019 | Aiden et al. | | |

FOREIGN PATENT DOCUMENTS

| | | |
|---|---|---|
| CN | 106687966 A | 5/2017 |
| CN | 107609350 A | 1/2018 |
| CN | 109411020 A | 3/2019 |
| WO | 2017214461 A1 | 12/2017 |

OTHER PUBLICATIONS

Luca Pireddu, Simone Leo, Gianluigi Zanetti, SEAL: a distributed short read mapping and duplicate removal tool, Bioinformatics, vol. 27, Issue 15, Aug. 2011, pp. 2159-2160 (Year: 2011).*

Nielsen, F. (2009). Linked Lists. In: A Concise and Practical Introduction to Programming Algorithms in Java. Undergraduate Topics in Computer Science. Springer, London (Year: 2009).*

Tischler, G., Leonard, S. biobambam: tools for read pair collation based algorithms on BAM files. Source Code Biol Med 9, 13 (2014). (Year: 2014).*

Panoiu, Manuela, et al. "An interactive learning environment for analyze linked list data structures." ICCCC 2006 (2006): 355. (Year: 2006).*

Arna Oskarsdottir, Gísli Másson, Páll Melsted, BamHash: a checksum program for verifying the integrity of sequence data, Bioinformatics, vol. 32, Issue 1, Jan. 2016, pp. 140-141, (Year: 2016).*

Hatem, M., & Ruml, W. (2013). External Memory Best-First Search for Multiple Sequence Alignment. Proceedings of the AAAI Conference on Artificial Intelligence, 27(1), 409-416. https://doi.org/10.1609/aaai.v27i1.8626 (Year: 2013).

Khalil, M. I. "A new heuristic approach for DNA sequences alignment." International Journal of Image, Graphics and Signal Processing 7.12 (2015): 18. (Year: 2015), 6 Pages.

Li, H., et al., "Fast and accurate short read alignment with Burrows-Wheeler transform", Bioinfomatics, Sequence analysis, vol. 25, No. 14, Feb. 20, 2009, 7 Pages.

* cited by examiner

*Primary Examiner* — Olivia M. Wise
*Assistant Examiner* — Jonathan Edward Hayes
(74) *Attorney, Agent, or Firm* — Slater Matsil, LLP

(57) ABSTRACT

In accordance with embodiments, a processing unit performs alignment of a short read (SR) against a reference genome sequence. The processing unit determines whether the SR is aligned. If the SR is not aligned, the processing unit receives the next SR and processes the next SR by repeating. If the SR is aligned, in response to the determination that the SR is aligned with the reference genome sequence at a first position in the reference genome sequence, the processing unit generates a new SR metadata entry corresponding to the SR. The processing unit finds a linked list in a SR metadata collection. The first position of the linked list in the SR metadata collection corresponds to the first position of the reference genome sequence where the SR is aligned. The processing unit performs duplicate marking based on the SR and the linked list.

12 Claims, 18 Drawing Sheets

Specification includes a Sequence Listing.

SEQUENCE LISTING

```
<160>  NUMBER OF SEQ ID NOS: 1

<210>  SEQ ID NO 1
<211>  LENGTH: 115
<212>  TYPE: DNA
<213>  ORGANISM: Unknown
<220>  FEATURE:
<223>  OTHER INFORMATION: Random sample sequence for the purpose of
       showing the file format to be read and processed by a computer

<400>  SEQUENCE: 1 cccaaagtgc tgggattaca ggcatgaggc accgcaccca gcctacattt tactgttact        60
gctagtattt gaatggtcct caatgtagtt caagctacaa tgaactcaag ttaca           115
```

MERGING DUPLICATE MARKING TO OPTIMIZE COMPUTER OPERATIONS FOR GENE SEQUENCING PIPELINE

CROSS-REFERENCE TO RELATED APPLICATIONS

This patent application is a continuation of PCT Patent Application No. PCT/CN2020/078903 filed Mar. 12, 2020 and entitled "Merging Duplicate Marking to Optimize Computer Operations for Gene Sequencing Pipeline," which claims the benefit of U.S. Provisional Patent Application No. 62/818,519 filed Mar. 14, 2019 and entitled "Merging Duplicate Marking to Optimize Computer Operations for Gene Sequencing Pipeline," the applications of which are hereby incorporated by reference as if reproduced in their entirety.

TECHNICAL FIELD

The present disclosure relates to efficient string matching, and, in particular embodiments, to systems and methods for improving computer operations of a gene sequencing system.

BACKGROUND

Matching a large quantity of characters can be technical challenging. For example, gene sequencing involves matching a huge amount of characters in multiple sub-systems of a gene sequencing system. A conventional gene sequencing system could take days on a single "bare metal server" (e.g., a single tenant physical server) to process a single input gene and consume at least hundreds of Gigabytes (GB) of storage space. Thus, techniques for improving computer operations of the gene sequencing system, particularly in terms of performance and storage resource utilization, are desired.

SUMMARY

In accordance with embodiments, a processing unit receives a count table and an occurrence table for a reference genome sequence generated using a Burrows Wheeler Transform (BWT) algorithm. The reference genome sequence comprises a sequence of base pairs (bps). The processing unit stores a first part of the occurrence table in a first type of memory. The size of the first part of the occurrence table is determined based on a size of the first type of memory and a first number of bps of short reads (SRs) to be processed using the first type of memory. The processing unit receives a short read (SR) of a sample sequence. The SR comprises the first number of bps and a second number of bps. The processing unit performs alignment of the short read (SR) against the reference genome sequence using the count table and the occurrence table. To perform the alignment, the processing unit may perform alignment of the first number of bps in the SR against the sequence of bps of the reference genome sequence using the first part of the occurrence table stored in the first type of memory.

In some embodiments, the processing unit may store a second part of the occurrence table in a second type of memory. The memory access time to the accessing the first part of the occurrence table in the first type of memory may be faster than the memory access time to the accessing the second part of the occurrence table stored in the second type of memory. The performing the alignment of the SR may further comprise performing alignment of the second number of bps in the SR against the sequence of base pairs of the reference genome sequence using the second part of the occurrence table stored in the second type of memory.

In some embodiments, the size of the first part of the occurrence table may be determined based on $$s = \left( \sum_{i=0}^{n-1} 4^{i+1} \right) \times 4.$$

s is a minimum number of bytes in the first type of memory. n is the first number of bps of short reads (SRs) to be processed using the first type of memory.

In some embodiments, the size of the first part of the occurrence table may be determined based on $$s = \left( \sum_{i=0}^{n-1} 4^{i+1} \right) \times 4 \times 2.$$

s is a minimum number of bytes in the first type of memory. n is the first number of bps of short reads (SRs) to be processed using the first type of memory.

In some embodiments, the occurrence table may comprise a plurality of rows. The number of the plurality of rows may equal the number of the sequence of bps in the reference genome sequence. A row of the occurrence table may comprise 4 entries of occurrence numbers corresponding to characters A, C, G, and T, respectively.

In some embodiments, the processing unit may initialize a top pointer to 0 and initialize a bottom pointer to a size of the reference genome sequence. Each of the top pointer and bottom pointer points to an entry in the occurrence table. The processing unit may determine the first part of the occurrence table based on $top_{new}$=count (char)+occurrence (to-$p_{old}$, char) and $bottom_{new}$=count (char)+occurrence (botto-$m_{old}$, char). Here, $top_{new}$ is a new value of the top pointer, $top_{old}$ is an old value of the top pointer, $bottom_{new}$ is a new value of the bottom pointer, $bottom_{old}$ is an old value of the bottom pointer, count (char) is a total count of characters that are smaller than character char, and occurrence (x, y) is an entry in the occurrence table indexed by row x and column y.

In some embodiments, the first part of the occurrence table stored in the first type of memory may comprise n levels of entries. Each entry of an i-th level of entries may have a $$\frac{1}{4^i}$$

memory access probability during the performing the alignment ($1 \leq i \leq n$). The n levels of entries of the first part of the occurrence table may have the highest memory access probabilities among all entries of the occurrence table.

In some embodiments, the count table may comprise four entries corresponding to four different bp types. Each entry of the count table may comprise a total count of bps in the reference genome sequence that are smaller than a bp corresponding to the each entry. The occurrence table may comprise a plurality of rows and four columns. The four columns may correspond to the four different bp types. Each entry of the occurrence table indexed by a row index and a column index may comprise a count of a bp corresponding to the column index up to the row index.

In accordance with embodiments, a processing unit performs alignment of a short read (SR) against a reference genome sequence. The reference genome sequence comprises a first sequence of base pairs (bps). The SR comprises a second sequence of bps.

The processing unit determines whether the SR is aligned against the reference genome sequence. If the SR is not aligned, the processing unit receives the next SR and processes the next SR by repeating. If the SR is aligned, in response to the determination that the SR is aligned with the reference genome sequence at a first position in the reference genome sequence, the processing unit generates an SR metadata entry corresponding to the SR.

The processing unit inserts the SR metadata entry to a linked list in a SR metadata collection. The position of the linked list in the SR metadata collection corresponds to the first position of the reference genome sequence where the SR is aligned.

In some embodiments, the SR metadata collection may be an array of linked lists. The size of the array may be based on a size of the first sequence of bps in the reference genome sequence. In some embodiments, the linked list may comprise one or more SR metadata entries after the inserting.

In some embodiments, the SR metadata entry may comprise an identifier (ID) of the SR. Before the performing the alignment of the SR, the processing unit may receive the SR from a plurality of SRs stored in a fastq file. The ID of SR may comprise an index of the SR in the plurality of SRs. The SR metadata entry may further comprise alignment results produced by the performing the alignment of the SR. The alignment results comprise a concise idiosyncratic gapped alignment report (CIGAR), a Flag, and a mark duplicate (MD) notation.

In some embodiments, the processing unit determines that alignment for all of the plurality of SRs stored in the fastq file has been performed. Then, the processing unit generates a binary alignment map (BAM) file based on the SR metadata collection without producing an intermediate sequence alignment map (SAM) file.

In accordance with embodiments, a processing unit performs alignment of a short read (SR) against a reference genome sequence. The reference genome sequence comprises a first sequence of base pairs (bps). The SR comprises a second sequence of bps.

The processing unit determines whether the SR is aligned against the reference genome sequence. If the SR is not aligned, the processing unit receives the next SR and processes the next SR by repeating. If the SR is aligned, in response to the determination that the SR is aligned with the reference genome sequence at a first position in the reference genome sequence, the processing unit generates a new SR metadata entry corresponding to the SR.

The processing unit finds a linked list in a SR metadata collection. The first position of the linked list in the SR metadata collection corresponds to the first position of the reference genome sequence where the SR is aligned. The processing unit performs duplicate marking based on the SR and the linked list.

In some embodiments, the SR may be in a pair end comprising the SR and a mate SR. The new SR metadata entry may comprise an average quality score (AQS) of quality scores of the bps in the SR. The new SR metadata entry may further comprise a PNEXT value indicating a distance between the first position of the linked list in the SR metadata collection and a second position of a second linked list in the SR metadata collection. The second linked list may comprise a second SR metadata entry corresponding to the mate SR. In some embodiments, the SR metadata entries in the linked list may be grouped based on PNEXT values of the SR metadata entries in the linked list.

In some embodiments, to perform duplicate marking, the processing unit may find a group of SR metadata entries in the linked list having the same PNEXT value as the new SR metadata entry. The processing unit may then find a head SR metadata entry in the group, wherein an AQS of the head SR metadata entry is the highest in the group. Next, the processing unit may mark one of the new SR metadata entry or the head SR metadata entry as duplicate based on a comparison between the AQS of the head SR metadata entry and the AQS of the new SR metadata entry. In some embodiments, if the AQS of the new SR metadata entry is higher than the AQS of the head SR metadata entry, the processing unit may mark the head SR metadata entry as duplicate. If the AQS of the new SR metadata entry is lower than the AQS of the head SR metadata entry, the processing unit may mark the new SR metadata entry as duplicate.

In some embodiments, the head SR metadata entry may be at the beginning of the group in the linked list. The processing unit may insert the new SR metadata entry at the beginning of the group if the AQS of the new SR metadata entry is higher than the AQS of the head SR metadata entry. The processing unit may insert the new SR metadata entry after the head SR metadata entry if the AQS of the new SR metadata entry is less than the AQS of the head SR metadata entry.

In some embodiments, the processing unit may generate a binary alignment map (BAM) file based on the SR metadata collection without producing an intermediate (sequence alignment map) SAM file or an intermediate unmarked BAM file (i.e., a BAM file without duplicate marking). In some embodiments, the SR metadata collection may be an array of linked lists. The size of the array may be based on the size of the first sequence of bps in the reference genome sequence.

The foregoing has outlined rather broadly the features of an embodiment of the present invention in order that the detailed description of the invention that follows may be better understood. Additional features and advantages of embodiments of the invention will be described hereinafter, which form the subject of the claims of the invention. It should be appreciated by those skilled in the art that the conception and specific embodiments disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawing, in which.

Corresponding numerals and symbols in the different figures generally refer to corresponding parts unless otherwise indicated. The figures are drawn to clearly illustrate the relevant aspects of the embodiments and are not necessarily drawn to scale.

DETAILED DESCRIPTION OF ILLUSTRATIVE EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

Figure 1A:
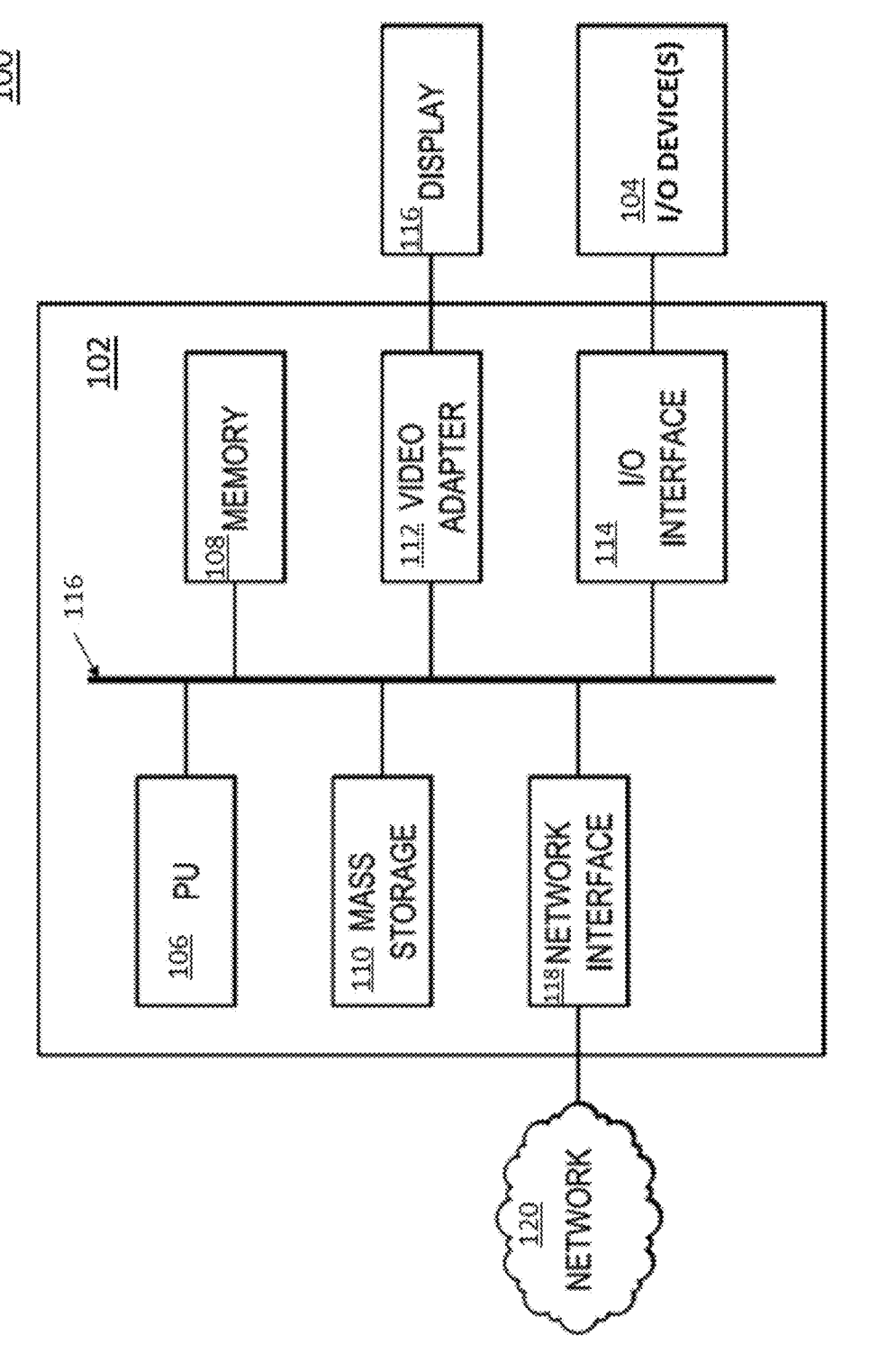
FIG. 1A illustrates a block diagram of a processing system that can be used for implementing the disclosed devices and methods, according to some embodiments.

FIG. 1A is a block diagram of a processing system 100 that can be used for implementing the devices and methods disclosed herein, according to some embodiments. Specific devices may utilize all of the components shown, or only a subset of the components, and levels of integration may vary from device to device. Furthermore, a device may contain multiple instances of a component, such as multiple processors, memories, transmitters, receivers, etc. The processing system 100 comprises a computing device 102 that includes multiple components, including a processing unit (PU) 106 that controls the overall operation of the computing device 102. The PU 106 is connected to and interacts with other components of the computing device 102, including one or more input/output devices 104, such as a speaker, microphone, touchscreen, keypad, mouse, keyboard, printer, display 110, and the like, memory 108, a mass storage device 110, a video adapter 112, and an I/O interface 114 via a bus 116.

The bus 116 may be one or more of any type of several bus architectures including a memory bus or memory controller, a peripheral bus, video bus, or the like. The PU 106 may comprise any type of electronic data processor, such as a central processing unit (CPU), a graphics processing unit (GPU), a tensor processing unit (TPU), and the like. The memory 108 may comprise any type of non-transitory system memory such as static random access memory (SRAM), dynamic random access memory (DRAM), synchronous DRAM (SDRAM), read-only memory (ROM), a combination thereof, or the like. In an embodiment, the memory may include ROM for use at boot-up, and DRAM for program and data storage for use while executing programs.

The mass storage device no may comprise any type of storage device configured to store data, programs, such as an operating system or applications, files, such as fasta and fastq files described below, and other information and to make the data, programs, and other information accessible via the bus 116. The mass storage device no may comprise, for example, one or more of a solid state drive, hard disk drive, a magnetic disk drive, an optical disk drive, or the like.

The video adapter 112 and the I/O interface 114 provide interfaces to couple external input and output devices to the computing device 102. As illustrated, examples of input and output devices include the display 116 coupled to the video adapter 112 and the mouse/keyboard/printer 104 coupled to the I/O interface. Other devices may be coupled to the computing device 102, and additional or fewer interface cards may be utilized. For example, a serial interface such as Universal Serial Bus (USB) (not shown) may be used to provide an interface for a printer.

The computing device 102 also includes one or more network interfaces 118, which may comprise wired links, such as an Ethernet cable or the like, and/or wireless links to access nodes or different networks 120. The network interface 118 allows the computing device 102 to communicate with remote units via the networks 120. For example, the network interface 118 may provide wireless communication via one or more transmitters/transmit antennas and one or more receivers/receive antennas. In an embodiment, the computing device 102 is coupled to a local-area network or a wide-area network for data processing and communications with remote devices, such as other computing devices, the Internet, remote storage facilities, or the like. The computing device 102 may be a part of a networked infrastructure that provides cloud services.

Although the processing unit 102 illustrated in FIG. 1A comprises the computing device 102, in alternative embodiments, the processing unit 100 may comprise a server that include one or more processing units, memory and mass storage. Not all components of the processing system 100 are required. A hardware device comprising one or more PUs coupled to one or more types memories may be used to implement the techniques disclosed herein. An example hardware device is described in more details in FIG. 5A below.

Gene sequencing refers to the procedure of comparing a deoxyribonucleic acid (DNA) sample against a unique commonly used reference genome. Every living creature has DNA. In one example of this disclosure, the focus can be on human gene sequencing.

DNA has the helix shape with two strands connected by base-pairs (bp). Base pairs (bps) are protein pairs of the following four types: Adenine (A), Thymine (T), Guanine (G), and Cytosine (C). The A protein type always pairs with the T protein type, and a G protein type always pairs with the C protein type. Accordingly, gene sequencing can reliably work with only one strand of the DNA.

Figure 1B:
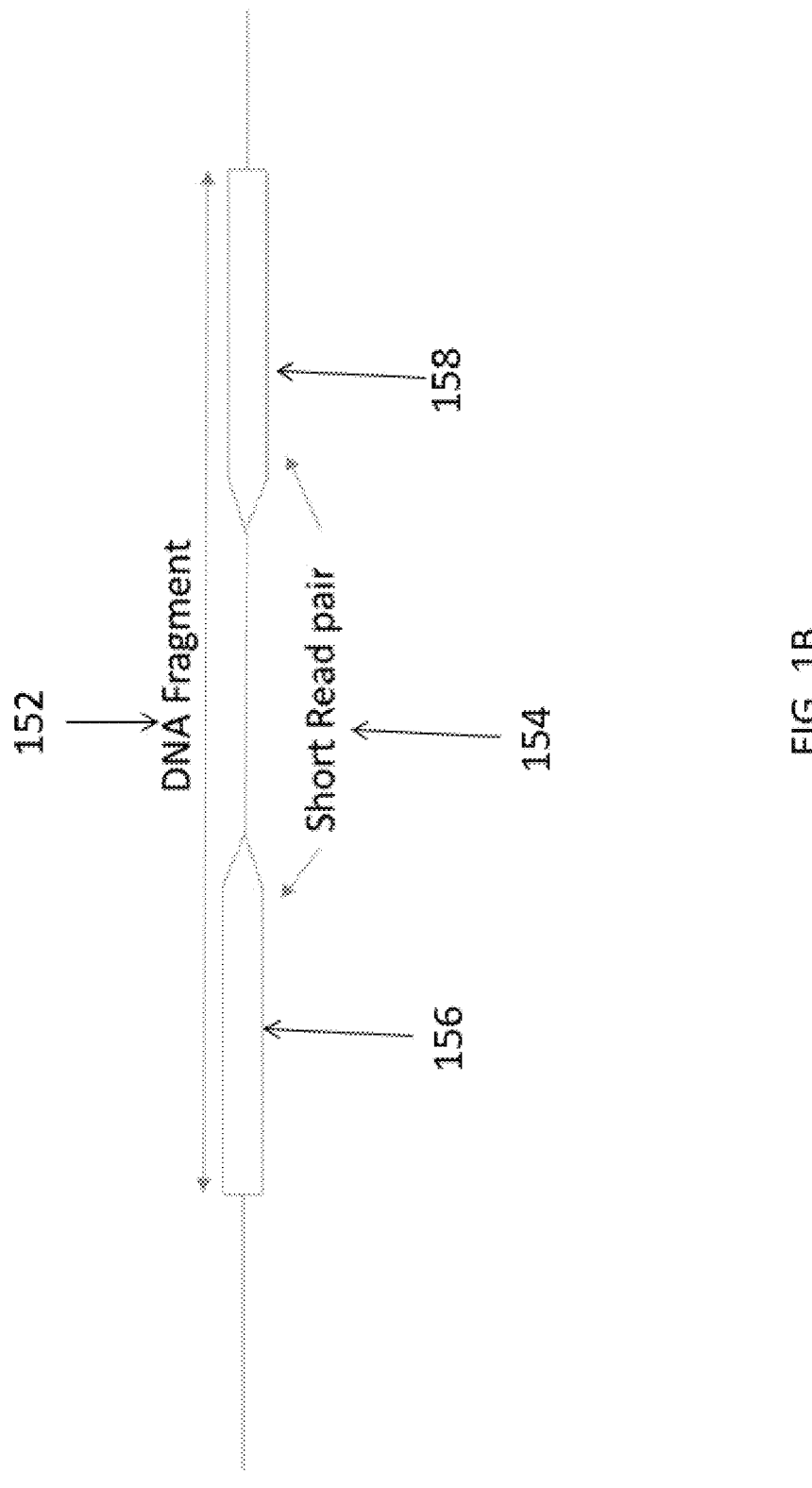
FIG. 1B shows a conceptual diagram of an SR pair.

There are 3.2 billion bps in a human genome, and the 3.2 billion bps are organized in 24 different chromosomes. Gene sequencers are usually used to chop a DNA input sample into small fragments (called DNA fragments) to create pairs of Short Reads (SRs). The output of a gene sequencer is millions of SR pairs stored in fastq files. Normally, all first pair-ends of the SR pairs (i.e., the first mates) are stored in one fastq file, and second pair-ends of the SR pairs (i.e., the second mates) are stored in a second fastq file. FIG. 1B shows a conceptual diagram of an SR pair 154. The SR pair 154 may be a part of a DNA fragment 152. The SR pair 154 comprises a first pair end 156 (i.e., the first mate) and a second pair end 158 (i.e., the second mate).

Figure 1C:
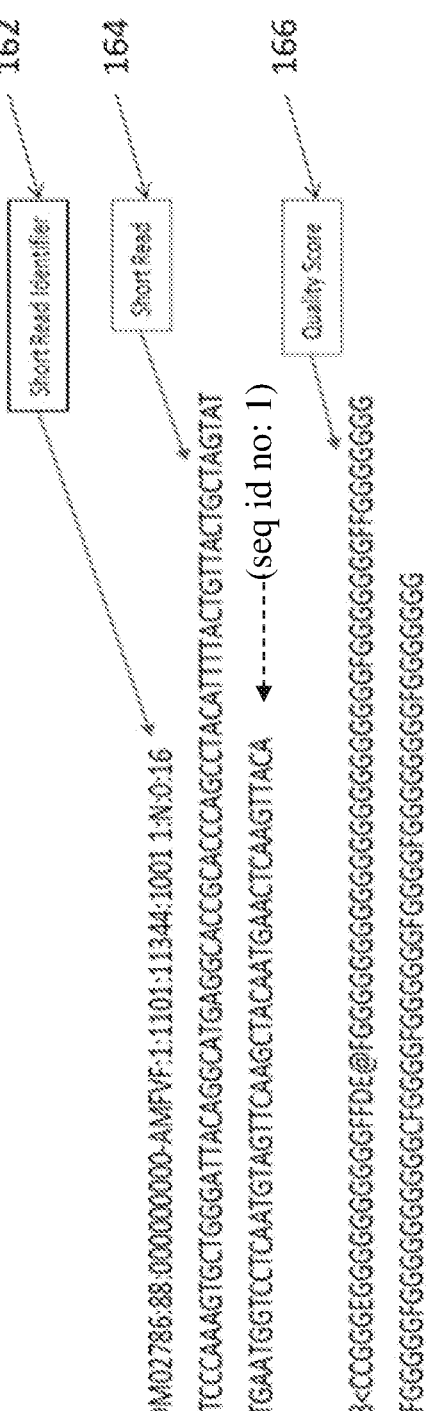
FIG. 1C illustrates a sample SR entry from a fastq file.

FIG. 1C shows a sample entry in a fastq file. Basically, each SR is specified with three elements in the fastq file: the SR identifier (ID) 162, the SR content 164, and the bp quality scores 166. The SR ID 162 is an arbitrary string assigned by the gene sequencer to each SR to uniquely identify an SR among other SRs. The SR content is the actual bp content of the SR, represented by characters such as A, T, G, C, or N (N means no type). The bp quality scores 166 are a string of characters. Each character represents a bp quality score associated with a corresponding bp in the SR.

The Sequence Listing (ASCII text file name: "Sample_ST25.txt," created Feb. 24, 2021, file size 775 bytes) corresponding to the sequence in FIG. 1C is hereby incorporated by reference.

Figure 2:
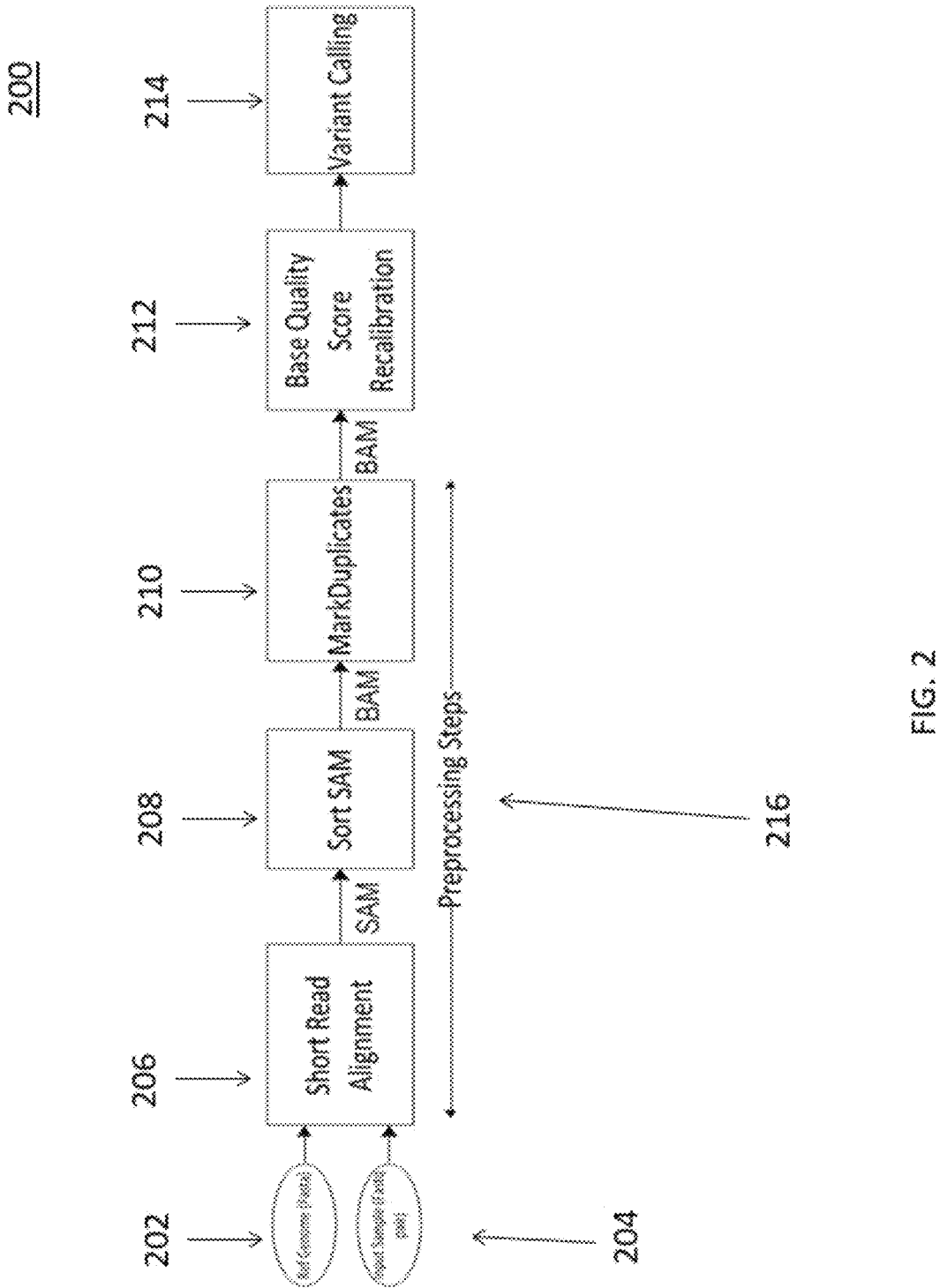
FIG. 2 illustrates a diagram of a gene sequencing system.

FIG. 2 shows a diagram of a gene sequencing system 200 (referred to as the system 200) implemented as Genome Analysis Toolkit (GATK). The system 200 is often used to find a matching between a reference genome sequence 202 and an input genome sample sequence 204. The reference genome sequence 202 is a string of bps of the reference genome. The input genome sample sequence 204 is string of bps of a DNA sample. The system 200 receives the reference genome sequence 202 in fasta file format and the input genome sample sequence 204 in fastq file format from a gene sequencer. The system 200, at the high level, consists of five sub-systems: the Short Read (SR) Alignment sub-system 206, the Sort Sequence Alignment Map (SAM) sub-system 208, the Mark Duplicates (MD) sub-system 210, the Base Quality Score Recalibration sub-system 212, and the Variant Calling sub-system 214. The SR Alignment sub-system 206 (or the aligner 206) is configured to align each SR relative to reference genome sequence 202 and provides the aligned SR in an output sequence alignment map (SAM) file. In other words, the SR Alignment sub-system 206 (or the aligner 206) finds the position of each SR relative to reference genome sequence 202. The SAM sub-system 208 is configured to receive the SAM file output by the SR Alignment sub-system 306, sorts all SRs in the SAM file based on the aligned positions of the SRs, and output all sorted and aligned SRs in a binary format of a SAM file (referred to as a BAM file). Thus, at the Sort Sequential Alignment (SAM) sub-system 208, all SRs are sorted based on their aligned positions. The Mark Duplicates sub-system 210 is configured to receive the BAM file and mark repetitive SRs in the BAM file as duplicate except for the SRs with the highest quality scores among each group of duplicates. Thus, at the Mark Duplicates sub-system 210, the repetitive SRs are marked as duplicate except for the ones with the highest quality scores among each group of duplicates. The quality scores are provided in the fastq file by the sequencer. In order to mark SRs as duplicate, the positions of both pair-ends of the SR pairs in the fastq files have to match first, and then the Average Quality Scores (AQSs) are compared. Consequently, except for the SR with the highest AQS, the rest SRs are marked as duplicate.

The first three sub-systems, the sub-systems 206, 208, and 210 are also collected referred to as the preprocessing sub-system 216 of the system 200. Various embodiment techniques in this disclosure aim to improve the performance and resource utilization (e.g., reduced storage space) of the three sub-systems in the preprocessing sub-system 216. After preprocessing by the preprocessing sub-system 216, the Base Quality Score Recalibration sub-system 212 recalibrates the quality scores when some of the quality scores are not accurate (i.e., any systematic errors introduced by the sequencer). The last sub-system of the system 200, the Variant Calling sub-system 214, finds the differences between input genome sample sequence 204 and reference genome sequence 202.

Referring again to FIG. 2, in some embodiments of the system 200, the SR Alignment sub-system 206 may be a first software program written in C, generally referred to in the art as a BWA-MEM software or tool (hereinafter BWA-MEM), whose instructions, when executed by the PU 106 of the computing device 102 causes the computing device 102 to find a position of each SR in the input genome sample sequence 204 relative to reference genome sequence 202 to find a position of each SR in the input genome sample sequence 204 relative to reference genome sequence 202. The SAM sub-system 208 and the Mark Duplicates sub-system 210 may be may be implemented as a second software program, written in Java, generally referred to in the art as a Picard software or tool. The Base Quality Score Recalibration sub-system 212 and the Variant Calling sub-system 214 may be implemented as a third software program written in Java, generally referred to in the art as a GATK software or tool. Each software program would be stored in mass storage, loaded into memory, and executed by a processing unit, such as the PU 106 of the computing device 102.

Overall, it could take days for a single computing device (e.g., computing device 102 such as a "bare metal server") to process a single input genome sample sequence 204 is generally desirable to reduce the amount of time required to process an input genome sample sequence 204. In addition, a tremendous amount of storage is required to store the intermediate data between sub-systems of the system 200. Therefore, technical solutions to computer operations of a gene sequencing system (or sub-systems of a gene sequencing system), particularly in terms of the performance improvement (i.e., reducing the overall processing time required by the system 200 to process an input genome sample sequence 204) and storage resource utilization of the gene sequencing system, are desired.

Some embodiment techniques target the SR Alignment sub-system 206. The SR Alignment sub-system 206 (i.e., the aligner 206) is the first sub-system of the system 200, and it relates to finding the position of each SR of the input genome sample sequence 204 in the reference genome sequence 202. The SR Alignment sub-system 206 is one of the most popular aligners in the system 200. BWA has three main sub-stages to align SRs to the reference genome sequence 202. The first sub-stage is referred to as seed generation (or "seeding") sub-stage. Seeds generated by the seed generation sub-stage are the sub-SRs that have at least one exact match in the reference genome sequence 202. The second sub-stage is referred to as chaining sub-stage, which puts seeds in close proximity together to create a chain. The third sub-stage is referred to as Smith-Waterman (SW) sub-stage and relates to finding the best alignments of seeds in chains in the reference genome sequence 202. Profiling results show that the seed generation sub-stage takes about 40% of the runtime of BWA. Because seed generation is very time-consuming, some embodiment techniques focus on improving the runtime of seed generation in the BWA at the SR Alignment sub-system 206.

For the SR Alignment sub-system 206, bp-to-bp comparison is not a feasible solution to find the true position of a SR in the reference genome sequence 202 because there are 3.2 billion bps in the reference genome sequence 202. The BWA-MEM implemented in the SR Alignment sub-system 206 in the gene sequencing system 200, follows a seed and extend strategy to align SRs of the input genome sample sequence 204 to the reference genome sequence 202. The BWA-MEM finds seeds, which are one or more portions of a SR of the input genome sample sequence 204 that exactly match the reference genome sequence 202, in the seeding sub-stage. Then, the seed and extend strategy extends around the seeds to embrace the whole SR in the final alignment result. The BWA-MEM often employs the Burrows Wheeler Transform (BWT) algorithm to find seeds.

The BWT is a transformation that rearranges the characters in a character string in such a way that the characters are all preserved (with the addition of an end-of-string character "\$"), but ordered for improved compressibility. The BWT is reversible, in that given the BWT of a string, the original string can be recovered algorithmically. The BWT algorithm uses the BWT of the reference genome to help search for a seed, given a SR. The BWT algorithm constructs two tables from the BWT of the reference genome sequence 202, and subsequently turns the search procedure into updating two pointer values that point to the occurrence table based on the bps in a SR and the entries of the two tables. The two tables are the count table and the occurrence table. The count table has four columns corresponding to the four possible bp types (A, T, G, and C). Each entry of the count table includes the number of characters (including the bps A, T, C and G, as well as the end-of-string character "\$") in the reference genome sequence 202 that are lexicographically smaller than that column bp. In the case of bps, the lexicographic order is A<C<G<T, with the end-of-string character "\$" being assigned the smallest lexicographic value (i.e., \$<A). The occurrence table, also called the BWT table, has as many rows as the size of the reference genome sequence 202 and four columns per each bp. Each entry represents the number of occurrences of that bp in the BWT of the reference genome sequence 202 up to the index corresponding to the entry.

The BWT algorithm starts the search with the last bp in the SR, and processes the SR bp-by-bp. It should be noted that, when using the following formulas to update the top and bottom pointers, the SR is traversed backwards (i.e., starting from the last bp). As shown in the Equations (1) and (2) below, as the search progresses, the BWT algorithm updates the two pointers, the top pointer and the bottom pointer, to the occurrence table entries, according to the value of the bp, the entry value from the count table indexed by the value of the bp, and the entry values from the occurrence table indexed by the value of the bp and the old values of the top and bottom pointers.

$$top_{new} = \text{count(char)} + \text{occurrence}(top_{old}, \text{char}) \qquad \text{Equation (1)}$$

$$bottomnew = \text{count(char)} + \text{occurrence}(bottomold, \text{char}) \qquad \text{Equation (2)}$$

where $top_{new}$ is the updated value of the top pointer, $top_{old}$ is the previous value of the top pointer, $bottom_{new}$ is the updated value of the bottom pointer, $bottom_{old}$ is the previous value of the bottom pointer, char is the character value of the current bp as the SR is being processed, count (x) looks up the count value of the character x in the count table, and occurrence (y, x) looks up the occurrence value of the character x at index y in the occurrence table. The value of the top pointer is initialized at 0 and the value of the bottom pointer is initialized as the largest index value in the occurrence table.

At each sub-system during the search, the gap (i.e., the interval, which is equivalent to the number of seed candidates) between the bottom and top pointers indicates the number of exact matches (also referred to herein as seed candidates) of that sub-SR in the reference genome sequence 202. The two pointers identify the intervals on the BWT of the reference genome sequence 202 with a match to a part of the SR. The search continues as long as the number of hits (i.e., the number of seed candidates) is greater than zero (i.e., the value of the bottom pointer is larger than the value of the top pointer) and there are more bps in the SR. The final result reflects the number of matches on the BWT of the reference genome sequence 202. Tables 1 and 2 below show the basic idea of string matching by monitoring the intervals indicating the number of matches. The example uses much smaller strings for illustration purpose. But, the same idea can be applied to long strings such as a reference genome sequence 202 which includes 3.2 billion bps. To find the number of matches of the string "CAT" (i.e., a SR) in a reference genome sequence comprising "ACGTTCATG," the BWT of the reference genome sequence comprising "ACGTTCATG" is first produced. In this example, the BWT of the reference genome sequence comprising "ACGTTCATG" is "G\$CTATCTAG". Table 1 below shows the occurrence table for the BWT of the reference genome sequence comprising "ACGTTCATG", and Table 2 shows the count table for the BWT of the reference genome sequence comprising "ACGTTCATG" (it may be noted that the count table is the same whether the count is performed for the BWT of the reference genome sequence comprising "ACGTTCATG" or for the reference genome sequence comprising "ACGTTCATG" itself)

TABLE 1

| | Occurrence Table | | | |
|---|---|---|---|---|
| Index | A | C | G | T |
| 0 | 0 | 0 | 0 | 0 |
| 1 | 0 | 0 | 1 | 0 |
| 2 | 0 | 0 | 1 | 0 |
| 3 | 0 | 1 | 1 | 0 |
| 4 | 0 | 1 | 1 | 1 |
| 5 | 1 | 1 | 1 | 1 |
| 6 | 1 | 1 | 1 | 2 |
| 7 | 1 | 2 | 1 | 2 |
| 8 | 1 | 2 | 1 | 3 |
| 9 | 2 | 2 | 1 | 3 |
| 10 | 2 | 2 | 2 | 3 |

TABLE 2

| Count Table | | | |
|---|---|---|---|
| A | C | G | T |
| 1 | 3 | 5 | 7 |

Using the formulas described above, the Occurrence Table 1 and the Count Table 2, the search based on Equations (1) and (2) will result in the Pointer Change Table 3 below.

TABLE 3

| Pointer Change Table | | |
|---|---|---|
| | Top Pointer | Bottom Pointer |
| Init | 0 | 10 |
| T | 7 | 10 |
| A | 2 | 3 |
| C | 3 | 4 |

Depending on the final values of the top pointer and the bottom pointer, the number of matches (i.e., seed candidates) is calculated as (bottom pointer–top pointer) if the bottom pointer>0 and the bottom pointer the top pointer; otherwise, the number of matches is 0. In the above example, there is one match (bottom pointer–top pointer=4–3=1). This means that one seed candidate is found for the SR "CAT" in the reference genome "ACGTTCATG". Further details of string matching using the count table, the occurrence table, and the top and bottom pointers can be found at "String Matching in Hardware Using the FM-Index," in Field-Programmable Custom Computing Machines (FCCM), 2011 IEEE 19th Annual International Symposium on, pp. 218-225, May 1-3, 2011, which is incorporated herein by reference in its entirety.

The above example is simplified for the purpose of illustration. In real-life application, the size of the data being processed may be very large. For example, a human reference genome sequence may be the reference genome sequence 202, and millions of SRs could be processed against one unique human reference genome. Human reference genome contains 3.2 billion base pairs (bps) and is read from storage (e.g., the mass storage no) and loaded into the system memory (e.g., the memory 108, usually double data rate (DDR) RAMs) at the beginning of the search process. Each SR is typically about 100-400 bps. Each SR is also read from the SR pool, which is usually a large file stored on storage (e.g., the mass storage no) and is loaded into the system memory (e.g., the memory 108). In some embodiments, a SR may be stored in a stack/cache, which is closer to the PU (e.g., the PU 106).

In the BWT algorithm, the occurrence and count tables are constructed at the start of the search procedure, and the BWT algorithm keeps using the two tables during the search.

Figure 3:
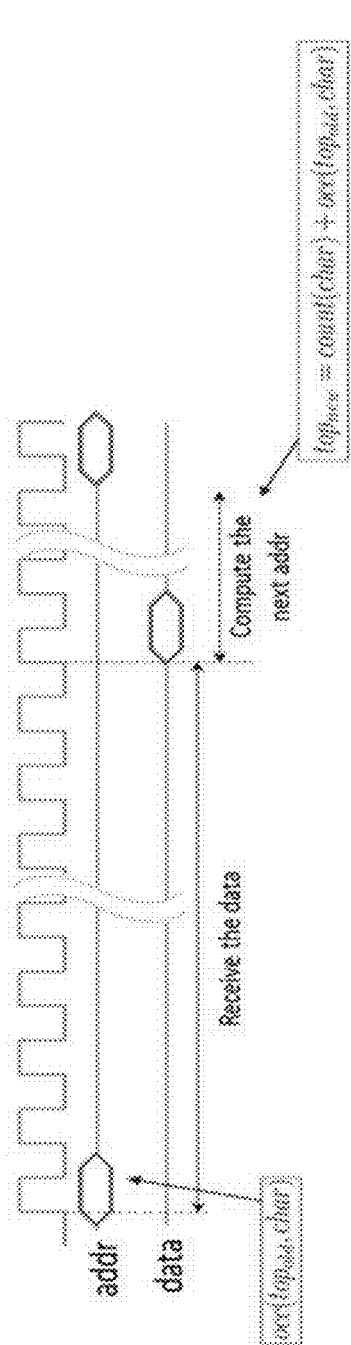
FIG. 3 illustrates a diagram of an example memory accesses pattern for a seeding search.

As illustrated in the above example, to process each bp in a SR, the BWT algorithm requires looking up the occurrence table twice—specifically at indices that depend on the values of the top and bottom pointers. The formulas for updating the top and bottom pointers result in pointer values that are updated in an unpredictable manner (e.g., not sequentially and not monotonically increasing or decreasing). There is no pattern to how the occurrence table (which is stored in memory, such as DDR RAM) should be accessed. The large size of the occurrence table (larger than the reference genome sequence itself) means that the occurrence table is usually kept in memory. The lack of pattern in how the occurrence table is accessed means that it is not possible to cache a portion of the occurrence table for faster access during the BWT algorithm (because it is not possible to anticipate which portion of the occurrence table will be needed). Instead, each access of the occurrence table to update the top or bottom pointer requires accessing the memory. The results is that the BWA-MEM memory-bound. The BWT algorithm accesses the occurrence table two times for processing each bp in the SR. If there are 200 bps in a SR, for example, 400 (2×200) memory accesses are required during the search procedure. However, accessing memory can be time-consuming, as illustrated in FIG. 3. The memory access patterns illustrated in FIG. 3 indicates what entries of each table (i.e., the occurrence table and the count table) are accessed. The count table is small and has a few entries only. So, accessing the count table would cause no or minimal memory accessing time concern. On the other hand, memory access time of the occurrence table can be very time-consuming due to the large size of the occurrence table.

As explained in the example above, the memory access pattern of the occurrence table is not only random but also dependent on the most recent content of the occurrence table entries read from the memory. That means, the random accesses are completely sequential. So the memory accesses cannot be pipelined. Consequently, this type of random memory access pattern slows down the whole processing time of the seeding sub-stage.

In some embodiments, the disclosed technique applies to a hardware (HW) device for the aligner. The focus of the disclosed technique is to bring the frequently accessed table entries and store these entries in a memory that has faster memory access time for the processing unit (i.e., the processing engine that performs the seeding sub-stage of the SR alignment sub-system 206). The disclosed technique would eliminate the need to access memory every time (twice per bp) in order to read the occurrence table's content from memory. Avoiding random and sequential memory accesses can reduce the time spent on memory accesses, which can then result in significant improvement of runtime of the SR alignment sub-system 206.

Figure 4:
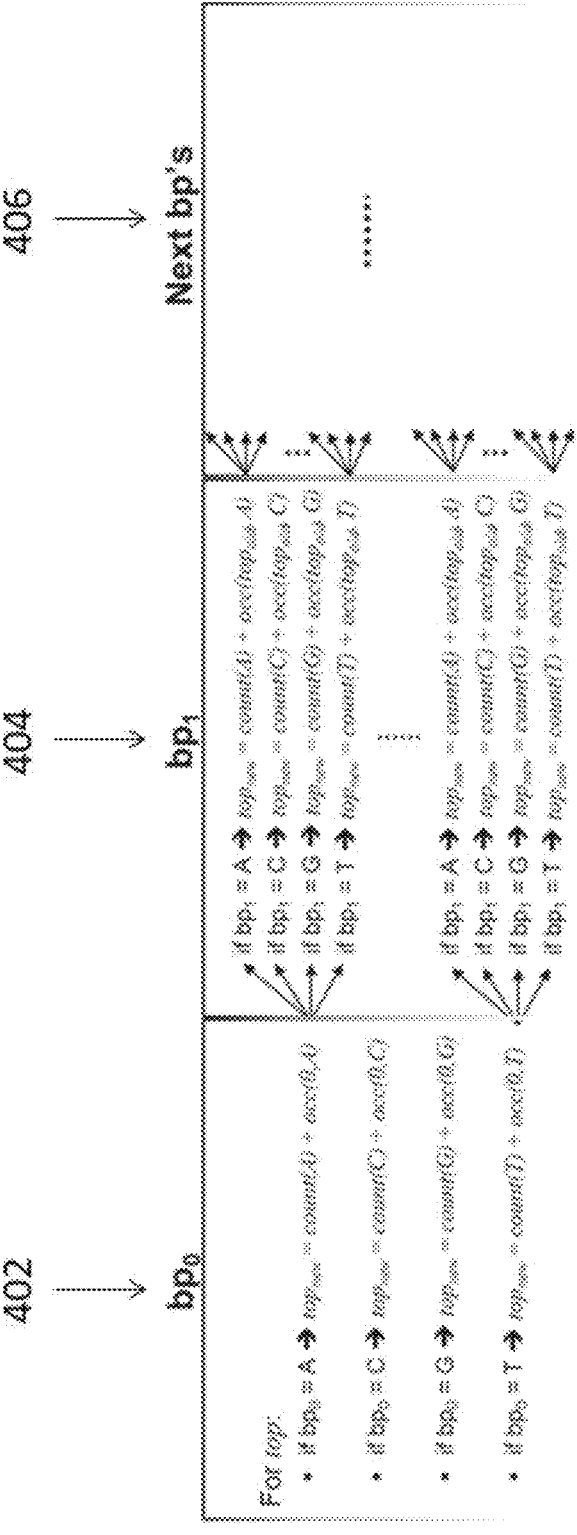
FIG. 4 illustrates a technique that utilizes the occurrence table's memory access patterns, according to some embodiments.

FIG. 4 illustrates an embodiment technique that utilizes the occurrence table's memory access patterns. Of the input SR of the input genome sample sequence 204, the very first bp, $bp_0$ 402, may be A, C, G, or T. For all possible $bp_0$, $top_{new}$ is calculated based on Equation (1), with $top_{old}$ being the initialized to 0. So for $bp_0$ 402, 4 entries of the occurrence table may be accessed. For the second bp, bp1 404, each of the 4 resulting $top_{new}$ from bp0 402 is used as the $top_{old}$ to calculate the $top_{new}$ for bp1 404. For example, if bp0 is A, 4 additional entries of the occurrence table may be accessed to calculate $top_{new}$ based on 4 possible values of bp1 (A, C, G, or T). If bp0 is T, another 4 additional entries of the occurrence table may be accessed to calculate $top_{new}$ based on four possible values of bp1 (A, C, G, or T). So, for bp1 404, 16 additional entries of the occurrence table may be accessed. For the bottom pointer, access patterns and $bottom_{new}$ for bp, can be calculated similarly based on Equation (2), with $bottom_{old}$ being the initialized to reference length for the first bp, $bp_0$.

In the BWA's seeding sub-stage, seed generation looks for matches between the reference genome sequence 202 and the SRs of the input genome sample sequence 204 from $bp_0$ of every single SR of the input genome sample sequence 204. That means, the search for seeds in every single SR of the input genome sample sequence 204 starts from $bp_0$ and goes through the same memory access pattern explained above. Therefore, BWA's seeding sub-stage will follow the same memory access patterns for all SRs of the input genome sample sequence 204. The present invention provides a hardware device for performing the seeding sub-stage of the SR alignment sub-system 206 that reduces the memory access patterns of the BWA's seeding sub-stage. If a specific part the occurrence table (the entries with the highest memory access probabilities) is stored in a type of memory that has faster memory access time for the processing unit that other type(s) of memory of the hardware device, seeding for all SRs of the input genome sample sequence 204 would benefit from the perspective of performance improvement.

One aspect of the disclose technique relates to speeding up the seeding sub-stage of the SR Alignment sub-system 206 by determining how much of the content of occurrence table entries can be stored in memory of a hardware (HW) device configured for performing the seeding sub-stage. In one embodiment, the amount of the content of occurrence table entries may be determined based on the amount of fast memory available on a HW device (i.e., the amount of memory that is located close to the processing unit of the HW device) and a number (n) of the first bps of the SRs to be processed (e.g., $bp_0$, $bp_1$, . . . , $bp_{n-1}$). FIG. 4 illustrates the calculation of the amount of storage required for each bp's look up in the occurrence table. For example, for the first level, bp, needs one of the possible 4 values stored on the very first row of the occurrence table (first column 402 in FIG. 4), meaning it needs (4)×4 Bytes (B) per entry=$4^1 \times$ 4B. For the next level, $bp_1$ needs one of the possible 16 values stored in the occurrence table (second column 402 in FIG. 4), meaning it needs (4)×16 B per entry=$4^2 \times$4B. In general, $bp_i$ needs one of $4^{i+1}$ entries. So, the memory requirement for $bp_i$ is $(4^{i+1}) \times$4B. In sum, the total memory required to store enough entries for the first n levels of bps would be $$\left( \sum\nolimits_{i=0}^{n-1} 4^{i+1} \right) \times 4B.$$

Factoring in the memory access patterns for the bottom pointer, the total memory required would be $$\left( \sum\nolimits_{i=0}^{n-1} 4^{i+1} \right) \times 4B \times 2.$$

Depending on the amount of fast memory available, the occurrence table entries for n levels of bps can be stored in the fast memory. The rest of the content of occurrence table entries can stay in other memory of the HW device that is further from the processing unit (i.e., the memory having slower access time by the processing unit of the HW device).

Figure 5A:
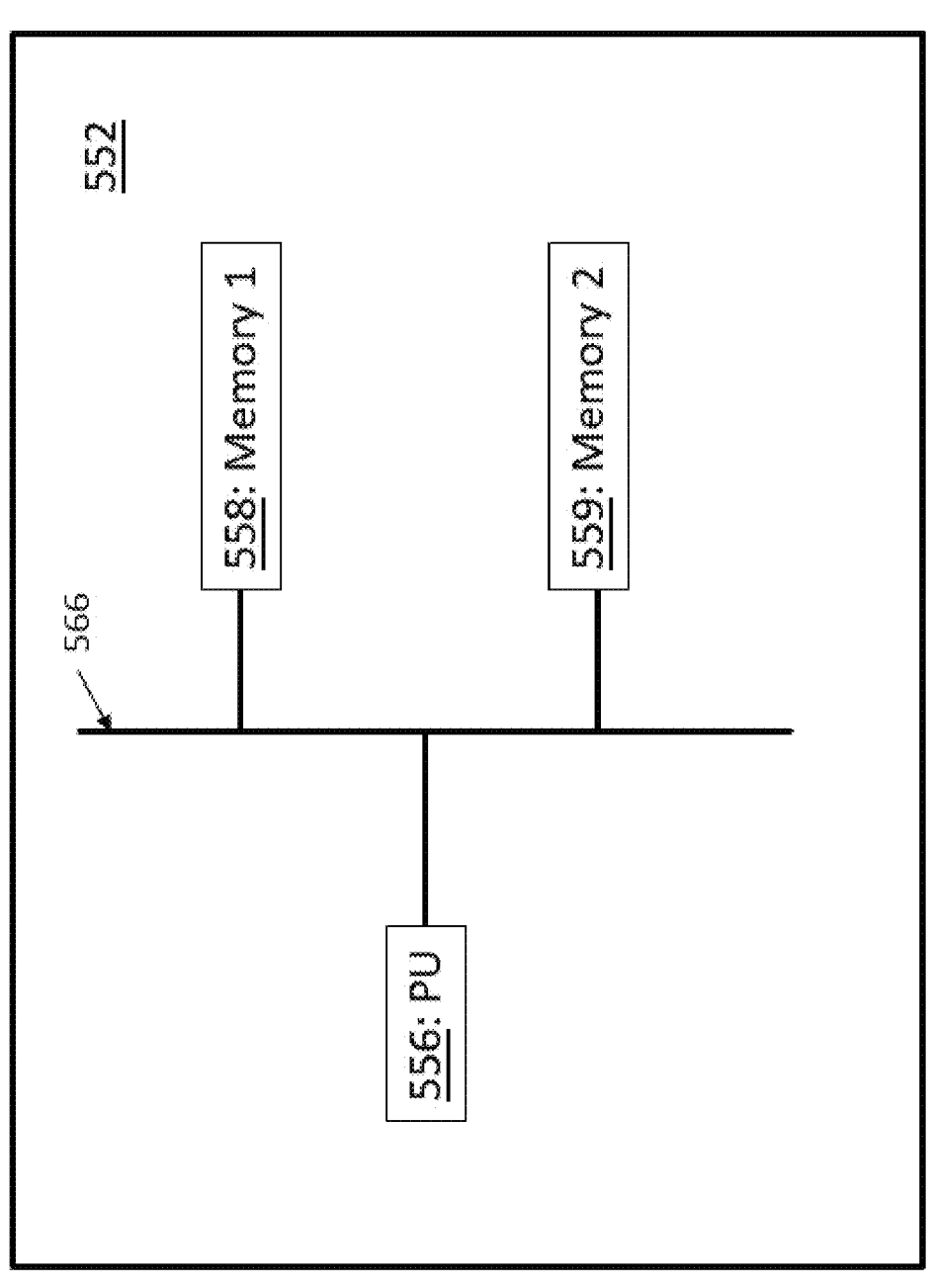
FIG. 5A illustrates a block diagram of a hardware device that can be used for implementing the disclosed methods, according to some embodiments.

FIG. 5A illustrates a block diagram of a hardware device 552 that can be used for implementing the disclosed methods, according to some embodiments. The hardware device 552 comprises a processing unit (PU) 556 that controls the overall operation of the hardware device 552. The PU 556 is connected to and interacts with at least two types of memories, such as a first type of memory 558 and a second type of memory 559, via a bus 566. The PU 556 may comprise any type of electronic data processor, such as a central processing unit (CPU), a graphics processing unit (GPU), a tensor processing unit (TPU), and the like. The memories 558 and 559 may comprise any type of non-transitory system memories such as static random access memory (SRAM), dynamic random access memory (DRAM), synchronous DRAM (SDRAM), read-only memory (ROM), a combination thereof, or the like. In an embodiment, the memories 558 and 559 may include ROM for use at boot-up, and DRAM for program and data storage for use while executing programs. In some embodiments, the first type of memory 558 may be smaller in size than the second type of memory 559, but the memory access time of the first type of memory 558 for the PU 556 may be faster than that of the second type of memory 559. The hardware device may be implemented as field programmable gate arrays (FGPA), application-specific integrated circuit (ASIC), or the like.

Figure 5B:
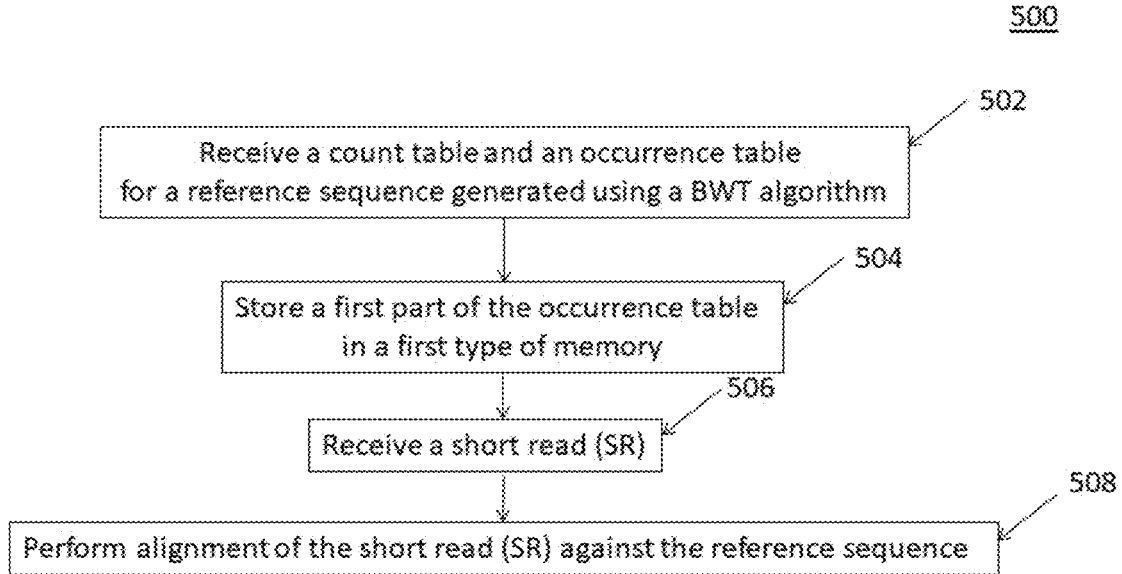
FIG. 5B shows a flowchart of a method for speeding up the seeding sub-stage of the SR Alignment sub-system, according to some embodiments.

FIG. 5B illustrates a flowchart of a method 500 for speeding up the seeding sub-stage of the SR Alignment sub-system 206, according to some embodiments. The method 500 may be carried out or performed by the processing unit (PU) 556 of the hardware device 552 as described with respect to FIG. 5A, or by the processing unit (PU) 106 of the computing device 102 as described with respect to FIG. 1. The computing device 102 stores computer-readable code or instructions of the SR alignment sub-system 206 executing on one or more PU(s) 106 of the computing device 102. The method 500 may be implemented by hardware, software, or a combination of hardware and software. Coding of the software for carrying out or performing the method 500 is well within the scope of a person of ordinary skill in the art having regard to the present disclosure. The method 500 may include additional or fewer operations than those shown and described and may be carried out or performed in a different order. Computer-readable code or instructions of the software executable by the one or more processing units may be stored on a non-transitory computer-readable medium, such as for example, the memory 108 of the computing device 102.

Method 500 starts at the operation 502, where the PU 106 receives a count table and an occurrence table for a reference genome sequence generated using a Burrows Wheeler Transform (BWT) algorithm. The reference genome sequence comprises a sequence of base pairs (bps). At the operation 504, the processing unit stores a first part of the occurrence table in a first type of memory. The size of the first part of the occurrence table is determined based on a size of the first type of memory and a first number of bps of short reads (SRs) to be processed using the first type of memory. At the operation 506, the processing unit receives a short read (SR) of an input sample genome sequence. The SR comprises the first number of bps and a second number of bps. At the operation 508, the processing unit performs alignment of the short read (SR) against the reference genome sequence using the count table and the occurrence table. To perform the alignment, the processing unit may perform alignment of the first number of bps in the SR against the sequence of bps of the reference genome sequence using the first part of the occurrence table stored in the first type of memory. The results of the method 500 are the seeds (i.e., sub-SRs that have at least one exact match in the reference genome sequence 202), which are the input to the chaining sub-stage and the SW sub-stage of the SR Alignment sub-system 206.

In some embodiments, the processing unit may store a second part of the occurrence table in a second type of memory. The memory access time to the accessing the first part of the occurrence table in the first type of memory may be faster than the memory access time to the accessing the second part of the occurrence table stored in the second type of memory. The performing the alignment of the SR may further comprise performing alignment of the second number of bps in the SR against the sequence of base pairs of the reference genome sequence using the second part of the occurrence table stored in the second type of memory.

In some embodiments, the size of the first part of the occurrence table may be determined based on $$s = \left(\sum_{i=0}^{n-1} 4^{i+1}\right) \times 4.$$

s is a minimum number of bytes in the first type of memory. n is the first number of bps of short reads (SRs) to be processed using the first type of memory.

In some embodiments, the size of the first part of the occurrence table may be determined based on $$s = \left(\sum_{i=0}^{n-1} 4^{i+1}\right) \times 4 \times 2.$$

s is a minimum number of bytes in the first type of memory. n is the first number of bps of short reads (SRs) to be processed using the first type of memory.

In some embodiments, the occurrence table may comprise a plurality of rows. The number of the plurality of rows may equal the number of the sequence of bps in the reference genome sequence. A row of the occurrence table may comprise 4 entries of occurrence numbers corresponding to characters A, C, G, and T, respectively.

In some embodiments, the processing unit may initialize a top pointer to 0 and initialize a bottom pointer to a size of the reference genome sequence. Each of the top pointer and bottom pointer points to an entry in the occurrence table. The processing unit may determine the first part of the occurrence table based on $top_{new}$=count (char)+occurrence (to-$p_{old}$, char) and $bottom_{new}$=count (char)+occurrence (bottom$_{old}$, char). Here, $top_{new}$ is a new value of the top pointer, $top_{old}$ is an old value of the top pointer, $bottom_{new}$ is a new value of the bottom pointer, $bottom_{old}$ is an old value of the bottom pointer, count (char) is a total count of characters that are smaller than character char, and occurrence (x, y) is an entry in the occurrence table indexed by row x and column y.

In some embodiments, the first part of the occurrence table stored in the first type of memory may comprise n levels of entries. Each entry of an i-th level of entries may have a $$\frac{1}{4^i}$$

memory access probability during the performing the alignment ($1 \leq i \leq n$). The n levels of entries of the first part of the occurrence table may have the highest memory access probabilities among all entries of the occurrence table.

In some embodiments, the count table may comprise four entries corresponding to four different bp types. Each entry of the count table may comprise a total count of bps in the reference genome sequence that are smaller than a bp corresponding to the each entry. The occurrence table may comprise a plurality of rows and four columns. The four columns may correspond to the four different bp types. Each entry of the occurrence table indexed by a row index and a column index may comprise a count of a bp corresponding to the column index up to the row index.

The disclosed embodiment techniques improve performance of computer operations of the gene sequencing system. For example, if the SR size is 100 bps and if the occurrence table entries for processing the first 20 bps can be stored in the allocated hardware cache (e.g., the first type of the memory), 20% of external, slower memory accesses would be eliminated. Fewer sequential random memory accesses can have a direct impact on improving the run-time of the SR alignment sub-system 206. As described above, the embodiment techniques can be applied to, but not limited to, a hardware platform. The embodiment techniques can also be applied to a SW platform.

Some gene sequencing systems align SRs in the input genome sample sequence 204 to the reference genome sequence 202 in the first processing sub-system (i.e., the SR Alignment sub-system 206) and stores the results in a sequence alignment map (SAM) formatted file which could take up to 300 to 500 GB for a large Whole Genome datasets. In some gene sequencing systems, the Sort SAM sub-system 208 (e.g. the second sub-system in the gene sequence system 200), starts sorting the results only after the alignment sub-system 206 is fully completed. Moreover, the Sort SAM sub-system 208 moves the entire aligned SR data around during the sort procedure, which often requires transferring some data to storage device (e.g., a hard drive) because the memory is not usually big enough to accommodate the whole data. These computer operations performed by the Sort SAM sub-system 208 are computationally expensive and I/O intensive. Consequently, these computer operations performed by the Sort SAM sub-system 208 are very time-consuming.

To further improve the computer operations of the gene sequencing system, some embodiment techniques aim to address the technical issues caused by the Sort SAM sub-system. For example, the Sort SAM sub-system starts to perform computer operations only after SR alignment is fully completed. Also, the alignment results are passed from the SR Alignment sub-system 206 to the Sort SAM sub-system 208 through a large SAM file which could take up to 500 GB of storage space. In addition, the Sort SAM sub-system performs computationally intensive I/O operations which could take several hours for processing systems (e.g. processing system 100) to process the large genome data sets.

To solve these technical issues, embodiment techniques, details of which described below, mitigate the run time of computer operations performed by the Sort SAM sub-system to improve the performance of computer operations of the gene sequencing system 200. In some embodiments, the disclosed techniques remove computer operations performed the Sort SAM sub-system completely, and integrate some computer operations performed by Sort SAM with some computer operations performed by SR Alignment Subsystem 206.

Figure 6:
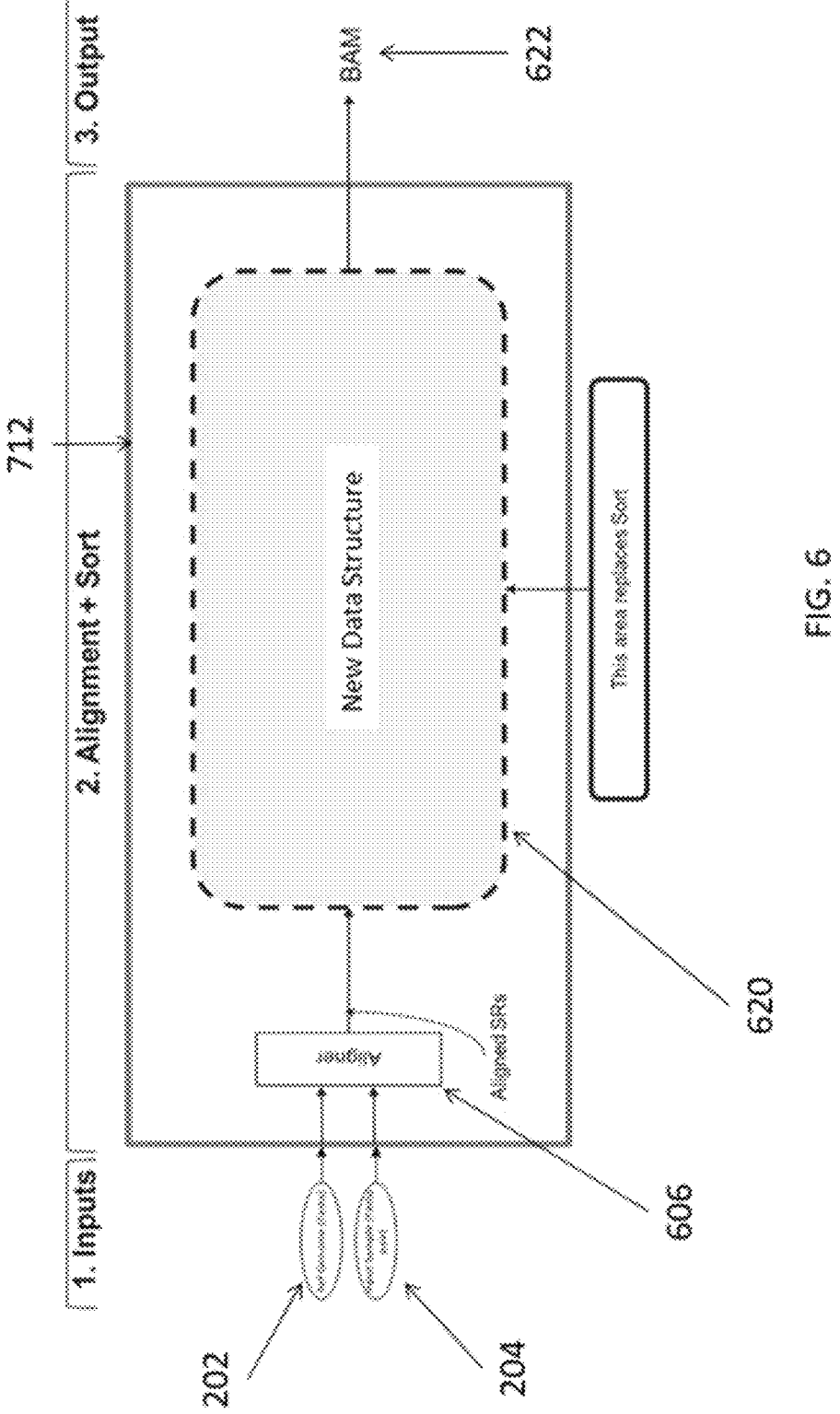
FIG. 6 shows a new sub-system of a new gene sequencing.

FIG. 6 illustrates a new sub-system that replaces the SR-Alignment sub-system 206 and the Sort SAM sub-system 208 of the system 200. The new sub-system (e.g. MergeAlignSort sub-system 712) is configured to receive a reference genome sequence 202 and an input genome sample sequence 204, perform a SR alignment operation (i.e., generates aligned SRs by aligning SRs in the input genome sample sequence 204 to the reference genome sequence 202) and a sorting operation in a more computationally efficient manner than the SR Alignment sub-system 206 and the Sort SAM-system 208 of system 200. The new MergeAlignSort sub-system 712 includes a SR aligner 606 that performs SR alignment and the new memory data structure 620 which is used to sort the aligned SRs before all the aligned SRs are generated. The new memory data structure 620 may have as many locations as the number of positions on a reference genome sequence 202. Once an SR of the input genome sample sequence 204 is aligned by the SR aligner 606 to the reference genome sequence 202, the aligned SR is stored in the memory location of the new data structure 620. The memory location corresponds to the alignment position of the SR on the reference genome sequence 202. In some embodiments, the new data structure 620 can be used to generate a BAM file 622 which is fed to the Mark Duplicates sub-system 210 (see FIG. 7).

Figure 7:
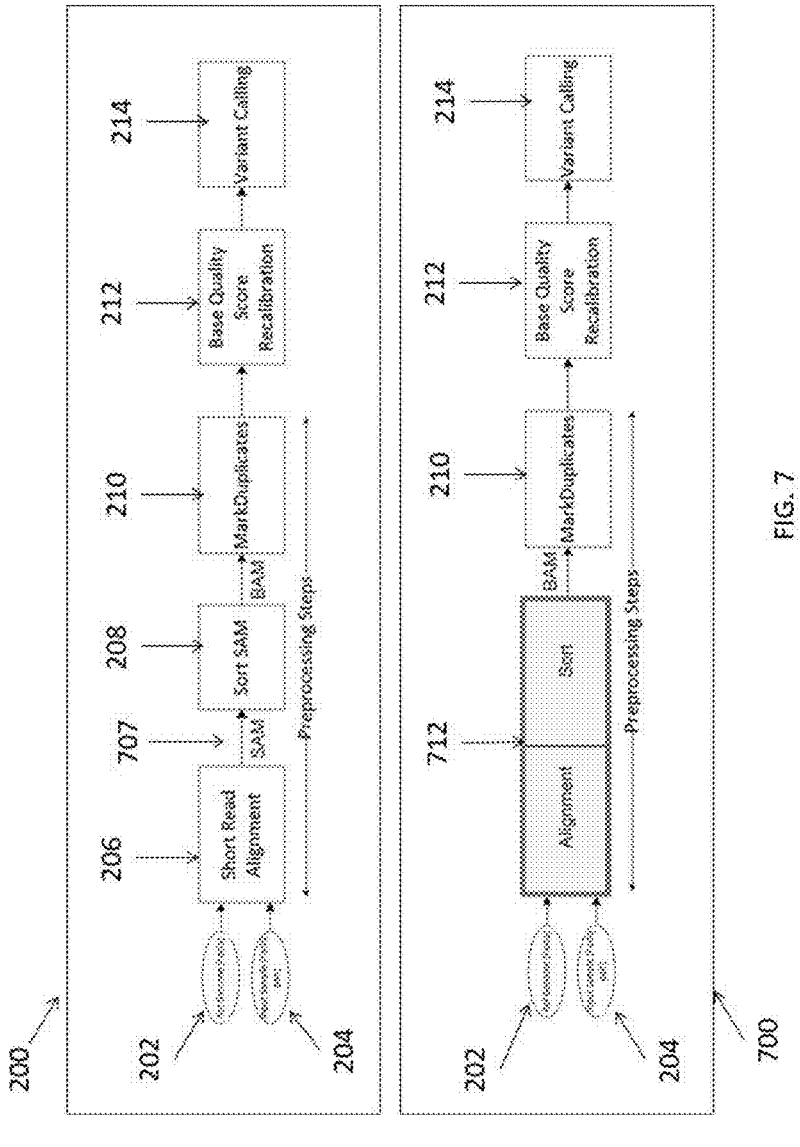
FIG. 7 illustrates the gene sequencing system of FIG. 2 and the new gene sequencing system.

FIG. 7 illustrates a comparison between the system 200 and a new gene sequence system 700 (hereinafter system 700) that includes the MergeAlignSort sub-system 712 of FIG. 6. As described above, in system 200, after the SR Alignment sub-system 206 completes generated aligned SRs (i.e., SR alignment), a Sort Sequence Alignment Map (SAM) file 707 is generated by the SR Alignment sub-system 206 and output to the Sort SAM sub-system 208. In contrast to the system 200, the system 700 does not generate a SAM file. Instead, the new memory data structure 620 of the MergeAlignSort sub-system 712 enables the operations of SR alignment and sorting performed by the SR Alignment sub-system 206 and the Sort SAM sub-system 208 of system 200, respectively, to be merged into one new SR alignment and sorting operation. The MergeAlignSort sub-system 712 is configured to perform one new align and sort operation to generate a BAM file, and output the BAM file.

In some embodiments, the new memory data structure 620 is a presorted data structure (i.e., a data structure in the memory) that stores aligned SRs generated by the aligner 606 as the aligned SRs are generated by the aligner 606. In some embodiments, the number of memory locations in the presorted data structure is equal to the number of positions on the reference genome sequence 202. Once the SR Alignment sub-system finds the position of a SR on the reference genome sequence 202, the MergeAlignSort sub-system 712 stores the alignment result information as SR metadata in the memory location of the presorted data structure, and the memory location corresponds to that aligned position of the SR in the reference genome sequence 202 (i.e., the position in the reference genome 202 at which the SR is aligned). As described in more detail below, the MergeAlignSort sub-system 712 may store essential alignment result information (i.e., an SR metadata) to decrease the amount of required memory to maintain the content of the presorted data structure.

In some embodiments, the new data structure comprises two main parts: a static part and a dynamic part. The static part may be an array with a fixed size. The fixed size of the array may be equal to the number of base pair positions of the reference genome sequence 202. Each array element holds the starting address of a linked list of SR metadata entries corresponding to the aligned SRs. The position of the array element in the array is the position on the reference genome sequence 202 at which the corresponding SRs are aligned. The dynamic part of the new data structure is linked lists that keep track of SRs that are aligned to each position on the reference genome sequence 202.

Often times, the whole input genome sample sequence 204 contains between 1 and 2 billion SRs. In theory, SRs would be aligned as being uniformly distributed to the 3.2 billion bp positions on the reference genome sequence 202, which indicates that, on average, each 2 consecutive base pair positions accommodate one aligned SR. Some real data analysis reveals that this may not be the case. Instead, there are several positions on the human reference genome to which multiple SRs are aligned. The dynamic part of the new data structure provides the flexibility to accommodate any arbitrary number of aligned SRs to each position on the reference genome sequence without consuming an extensive amount of memory.

Figure 8:
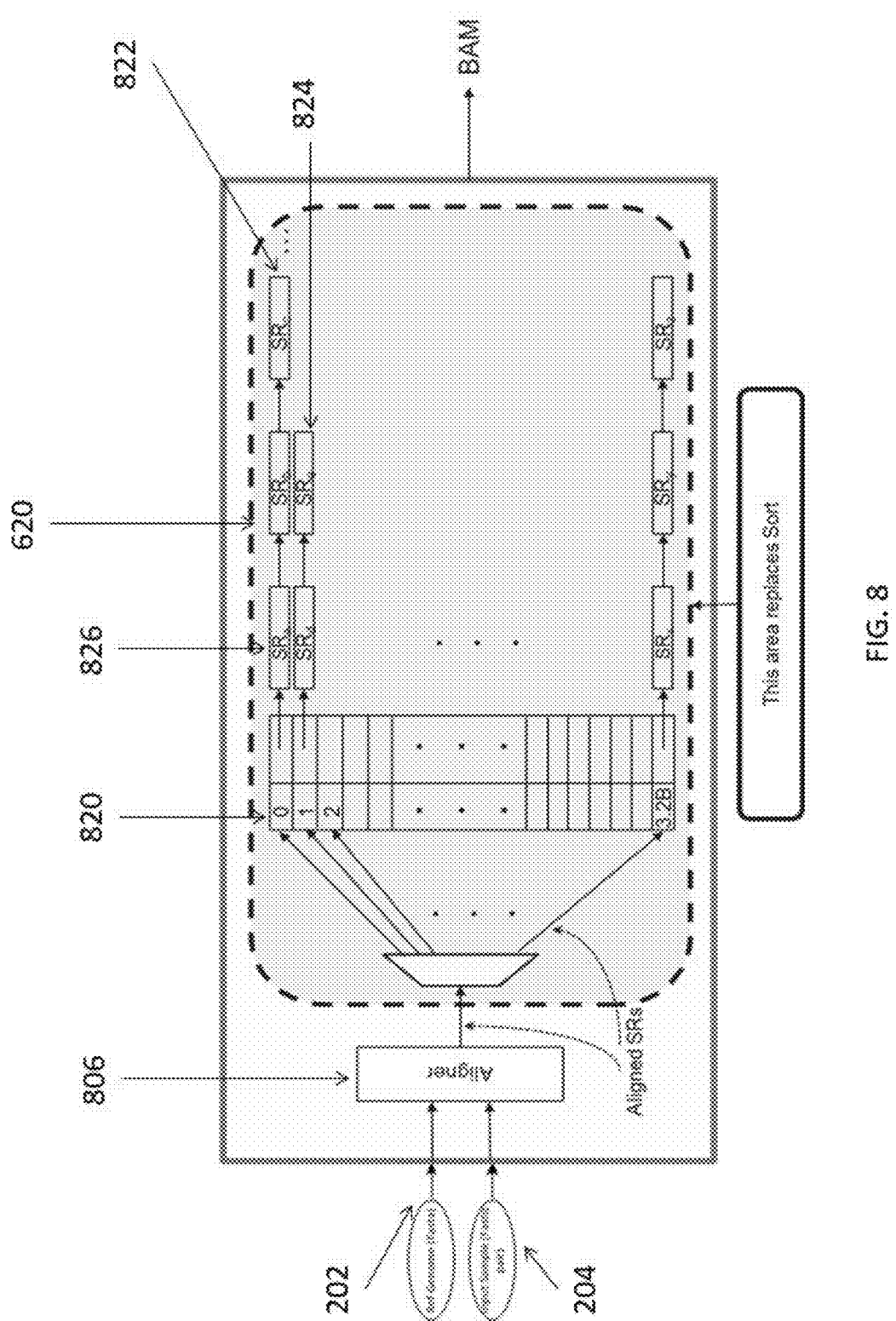
FIG. 8 illustrates a conceptual diagram of an embodiment of a new memory data structure included in the new sub-system FIG. 6, according to some embodiments.

FIG. 8 shows a conceptual diagram of an embodiment of the new memory data structure 620 of FIG. 6, according to some embodiments. There are two main components to the data structure 620. The first component is a static array 820 of memory locations which stores the starting address of linked lists for the aligned SRs. So, the linked lists, such as linked lists 822 and 824, are the second components of the new data structure 620. The number of locations in this static array 820 may be equal to the number of positions on the reference genome sequence. When the SR Aligner 806 finds the alignment position of an SR, an SR metadata entry is added to the corresponding location of the static array 820. If no previous SR is aligned to that position, a new linked list is initialized and added to the position of the static array 820. If a linked list is already constructed for that position, the new aligned SR will be inserted to the linked list.

For example, the array element 0 of the static array 820 stores the starting address of the linked list 822. The linked list 822 contains SR metadata entries corresponding to SRs such as $SR_a$, $SR_b$, and $SR_c$, and so on. $SR_a$, $SR_b$, and $SR_c$ are aligned at the position 0 on the reference genome sequence. So, SR metadata entries corresponding to $SR_a$, $SR_b$, and $SR_c$ are stored as a part of the linked list 822 pointed by the array element 0 of the static array 820. Similarly, the array element 1 of the static array 820 stores the starting address of the linked list 824. The linked list 824 contains SR metadata entries corresponding to SRs such as $SR_d$ and $SR_e$. $SR_d$ and $SR_e$ are aligned at the position 1 on the reference genome sequence. So, SR metadata entries corresponding to $SR_d$ and $SR_e$ are stored as a part of the linked list 824. In general, the array element 1 of the static array 820 stores the starting address of the linked list i, and the linked list i contains SR metadata entries corresponding to one or more SRs that are aligned at the position i on the reference genome sequence. Because of the dynamic structure of aligned SR metadata linked lists, there is no limitation on the number of SRs that could be kept at each memory location.

Each SR metadata entry, such as SR metadata entry 826 corresponding to $SR_a$ of the new data structure may store an identifier (ID) to identify the corresponding aligned SR, such as the SR identifier 162 shown in FIG. 1C. In some embodiments, to further improve performance and memory resource utilization, a new indexing scheme may be utilized to avoid carrying around the SR identifiers 162. The SRs may be enumerated based on the order in which the SRs appear in the fastq file. Accordingly, an SR identifier 162 may be replaced with an index. By allocating 4 Bytes to the index field, up to 4 billion SRs can be identified. Such indexing technique is more efficient than preserving SR identifiers in the fastq file, which could be any arbitrary string of any size. Furthermore, the disclosed indexing technique is simple, and retrieving SRs having indexes as the IDs is straightforward, which in turn improves the performance of computer operations of the gene sequencing system.

For the static part (e.g., the array 820) of the new data structure 620, 4 Bytes (B) may be needed per memory location to be able to address possible SR metadata entries corresponding to more than 4 billion SRs. For example, there may be 3.2 billion bp positions on a human reference genome. So, static part (e.g., the array 820) of the new data structure 620 may need the same number of location, and the total amount of required memory for static part can be 12.8 GB (3.2 billion×4 B=12.8 GB).

Each SR metadata entry corresponding to an SR may need 14 Bytes to store the alignment result for that SR. In some embodiments, the SR metadata entry does not need to keep the SR content or the bp quality score information because the index ID allows the embodiment techniques to retrieve the corresponding SR content from the fastq file. The rest of SR metadata entry may store the essential alignment results. In one example embodiment, an SR metadata entry may need 4 Bytes to store the index ID and 10 Bytes to store the alignment results. The alignment results may include a CIGAR (Concise Idiosyncratic Gapped Alignment Report) which is a compressed representation of an alignment, a Flag, and a Mark Duplicates (MD) notation.

The amount of required memory for the dynamic part depends on the number of SRs in the input genome sample sequence 204. When a whole genome sample sequence has 2 billion SRs, which is a fairly big data input in the context of gene sequencing, 28 GB of memory may be needed for the dynamic part.

So, a total of 40.8 GB of memory may be required to store both the static and the dynamic parts of the data structure 620. The amount of memory available nowadays on typical computer systems for gene sequencing can be well above 100 GB. The required memory for the new data structure 620 could be allocated for most computer systems.

In some alternative embodiments, the first component 820 of the data structure 620 may be dynamic (e.g., a linked list). In some alternative embodiments, the second component (822, 824, . . . ) of the data structure 620 may be static (e.g., an array).

Figure 9:
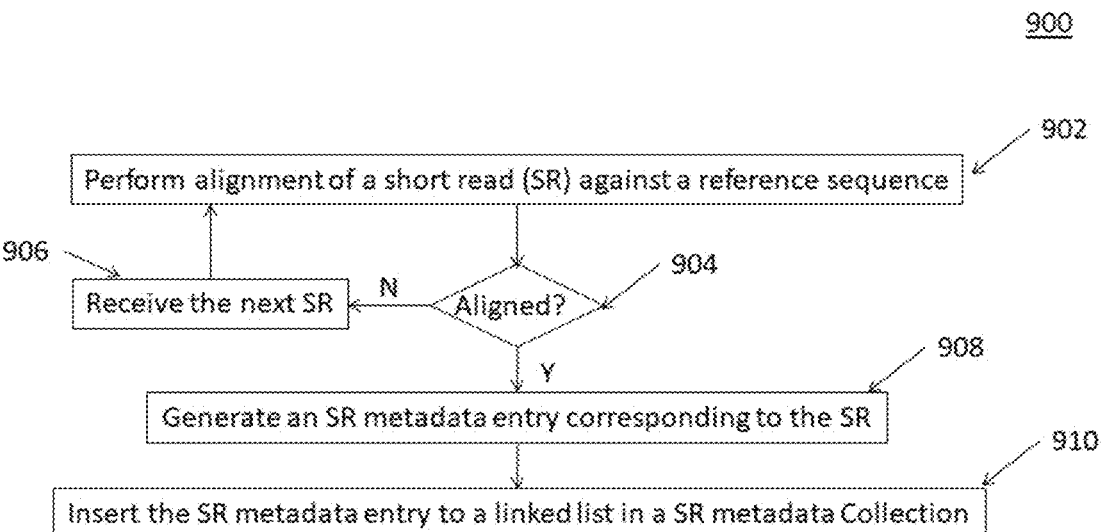
FIG. 9 shows a flowchart of a method performed by the new sub-system of FIG. 6 according to some embodiments.

FIG. 9 illustrates a flowchart of a method 900 performed by MergeAlignSort sub-system 712 according to some embodiments. The method 900 may be carried out or performed by a processing unit of a computing device described above, such as the PU 106 of the computing device 102, as described with respect to FIG. 1. Additional examples of the processing units 106 may include, but are not limited to, central processing units (CPUs), graphics processing units (GPUs), tensor processing units (TPUs), application-specific integrated circuits (ASCIs), field-programmable gate arrays (FPGAs), artificial intelligence (AI) accelerators, or combinations thereof. The computing device 102 may include computer-readable code or instructions executing on one or more processing units of a processing system, such as the processing units 106 of the computing device 102 of the processing system 100 as described with respect to FIG. 1. The method 900 may be implemented by hardware, software, or a combination of hardware and software. Coding of the software for carrying out or performing the method 900 is well within the scope of a person of ordinary skill in the art having regard to the present disclosure. The method 900 may include additional or fewer operations than those shown and described and may be carried out or performed in a different order. Computer-readable code or instructions of the software executable by the one or more processing units may be stored on a non-transitory computer-readable medium, such as for example, the memory 108 of the computing device 102.

Method 900 starts at the operation 902, where the processing unit performs alignment of a short read (SR) against a reference genome sequence 202. The reference genome sequence 202 comprises a first sequence of base pairs (bps). The SR comprises a second sequence of bps.

At the operation 904, the processing unit determines whether the SR is aligned against the reference sequence. If the SR is not aligned, the processing unit receives the next SR at the operation 906 and processes the next SR by repeating at the operation 902. If the SR is aligned, in response to the determination that the SR is aligned with the reference genome sequence 202 at a first position in the reference genome sequence 202, the processing unit generates an SR metadata entry corresponding to the SR at the operation 908.

At the operation 910, the processing unit inserts the SR metadata entry to a linked list in a SR metadata collection. The position of the linked list in the SR metadata collection corresponds to the first position of the reference genome sequence 202 where the SR is aligned.

In some embodiments, the SR metadata collection may be an array of linked lists. The size of the array may be based on a size of the first sequence of bps in the reference sequence. In some embodiments, the linked list may comprise one or more SR metadata entries after the inserting.

In some embodiments, the SR metadata entry may comprises an identifier (ID) of the SR. Before the performing the alignment of the SR, the processing unit may receive the SR from a plurality of SRs stored in a fastq file. The ID of SR may comprise an index of the SR in the plurality of SRs. The SR metadata entry may further comprise alignment results produced by the performing the alignment of the SR. The alignment results comprise a concise idiosyncratic gapped alignment report (CIGAR), a Flag, and a mark duplicate (MD) notation.

In some embodiments, the processing unit determines that alignment for all of the plurality of SRs stored in the fastq file has been performed. Then, the processing unit generates a binary alignment map (BAM) file based on the SR metadata collection without generating an intermediate sequence alignment map (SAM) file.

By utilizing a new memory data structure 620, the disclosed embodiments resolve the technical issue of multiple aligned SRs having the same aligned position with faster run time and less memory requirement. The new memory data structure 620 allows the aligner 606 to store alignment results to their pre allocated location, which eliminates the Sort SAM sub-system 208 in a gene sequencing system.

Figure 10:
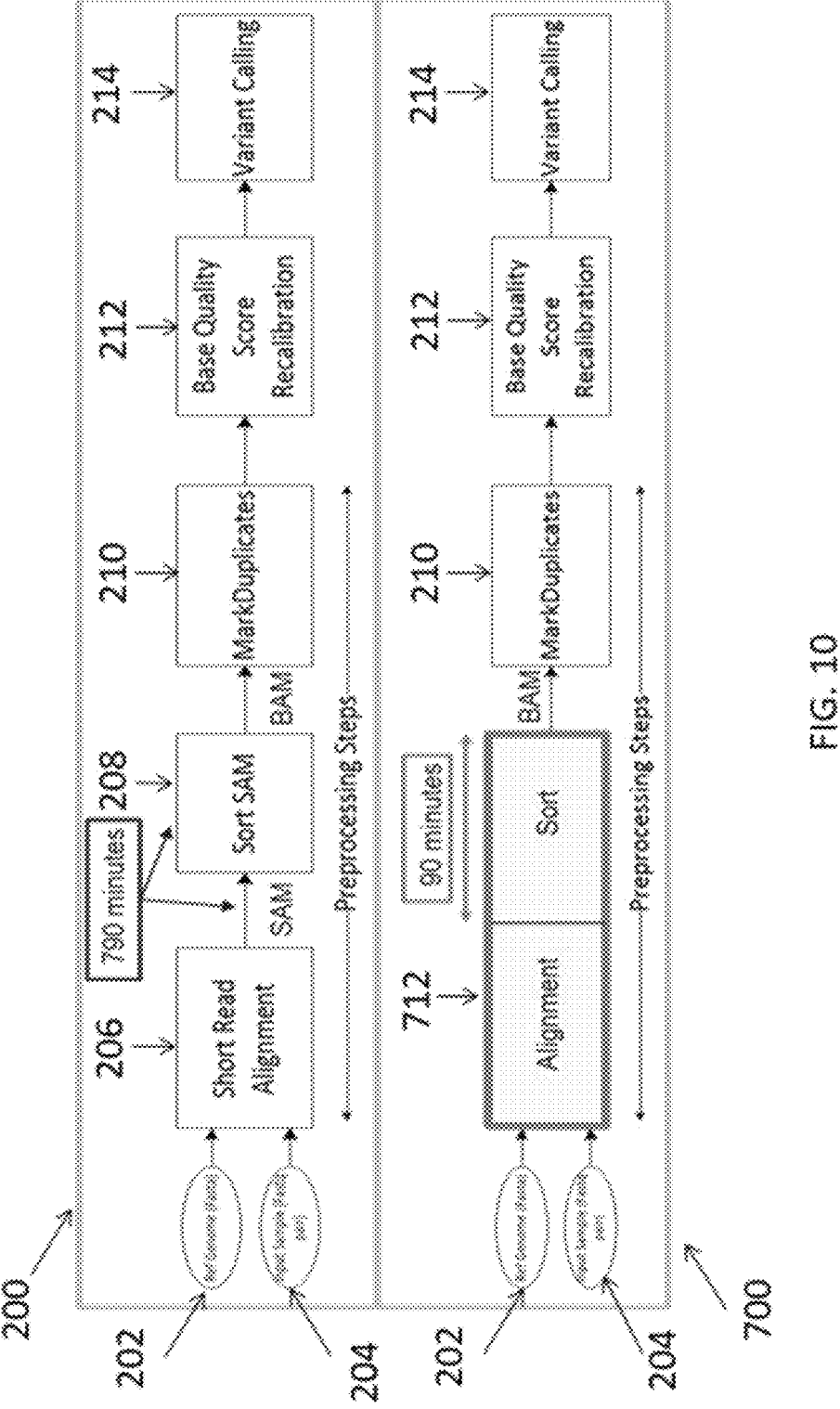
FIG. 10 illustrates the run time improvement of the new sub-system of FIG. 6 over the Sort SAM sub-system of the gene sequencing system shown in FIG. 2.

FIG. 10 shows the run time improvement of the computer operations performed by the MergeAlignSort sub-system 712 over the computer operations performed by Sort SAM sub-system 208. In some testing environments for comparing the runtime of the Sort SAM sub-system 208 (e.g. the time it takes the Sort SAM sub-system 208 to perform the sorting computer operations) to the runtime of the MergeAlignSort 712 sub-system (e.g., the time it takes for the MergeAlignSort sub-system 712 to perform the alignment and sorting operations, the runtime of the Sort SAM sub-system 208 in the gene sequencing system 200 may be 790 minutes. In contrast, the runtime of the disclosed MergeAlignSort sub-system 712 is reduced to around 90 minutes by replacing the Sort SAM I/O and processing operations with using the new data structure 620 and merging the alignment operations and the sort operations performed by two sub-systems (e.g. the SR Alignment sub-system 206 and the Sort SAM sub-system 208) into one combined sub-system (e.g., MergeAlignSort sub-system 712) the where the sort operations can be performed concurrently with aligner 606.

In addition, with disclosed MergeAlignSort embodiments, there is no need to transfer alignment results in the form of a SAM file from the SR alignment sub-system 206 to the Sort SAM sub-system 208. The size of a SAM file for a regular genome dataset could range from 300 to 500 GB. The disclosed new sub-system (e.g., the MergeAlignSort sub-system 712) eliminates such storage space requirement, which result in better storage resource utilization and performance improvement.

Furthermore, the disclosed new sub-system (e.g., MergeAlignSort sub-system 712), particularly the use of the new data structure 620 could facilitate further optimization of the next processing sub-systems (e.g., the Mark Duplicates sub-system 210) along the gene sequencing system 200 by exploiting the features that the new data structure 620 provides.

For example, some embodiments of this disclosure further utilize the new data structure 620 to improve the performance over the Mark Duplicates sub-system 210. As described above, the Mark Duplicates sub-system 210 marks the repetitive SRs as duplicate except for the ones with the highest quality scores among each group of duplicate SRs. The quality scores are provided by the sequencer in the fastq file. In order to mark SRs as duplicate, the positions of both pair-ends of the SR pairs in the fastq files have to match first, and then the Average Quality Scores (AQSs) are compared. Consequently, except for the SR with the highest AQS, the rest are marked as duplicate. In the system 200 shown in FIG. 2, the output of the Sort SAM sub-system 208 is written into an intermediate BAM file (without duplicate marking). The BAM file is then used as an input to the Mark Duplicates sub-system 210. The output of the Mark Duplicates sub-system 210 is another BAM with duplicate markings.

There are several technical issues in the Mark Duplicates sub-system 210. A typical BAM file takes between 80 GB and 120 GB of storage space. So, writing of the BAM file is time consuming. In addition, the Mark Duplicates sub-system 210 has to wait until the Sort SAM sub-system 208 completes before it can start the MD operations. Also, the Mark Duplicate sub-systems 210 needs to find duplicates globally, which means the Mark Duplicates sub-system 210 has to go through all SRs in order to find duplicates.

To further optimize computer operations of the system 200, some embodiment techniques merge the Mark Duplicates sub-system with the MergeAlignSort sub-system by further utilizing the new data structure 620 described above. In so doing, the intermediate BAM file generated by the Sort SAM sub-system 208 can be eliminated. The Mark Duplicates (MD) operations can start as soon as the first SR is aligned and sorted. This reduces the wait time on the Mark Duplicates side. The MD may find duplicates locally and as soon as the first SR is sorted. The global duplicated SRs would be found as the MD operations progress.

Figure 11:
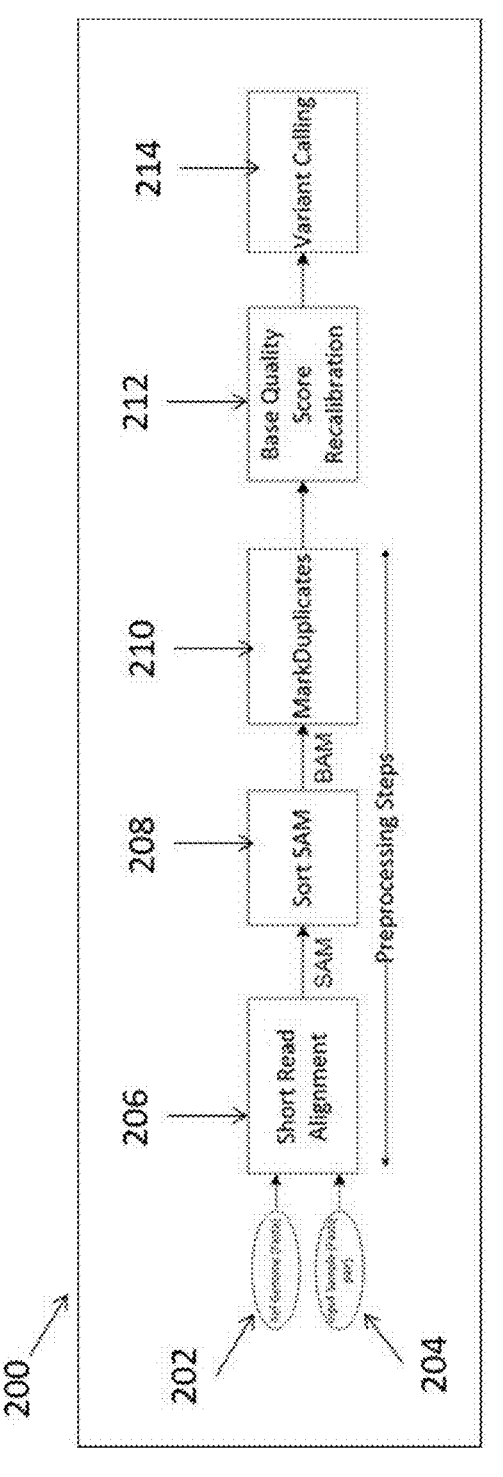
FIG. 11 illustrates the gene sequencing system of FIG. 2 and a second new gene sequencing system according to some embodiments.
Figure 11:
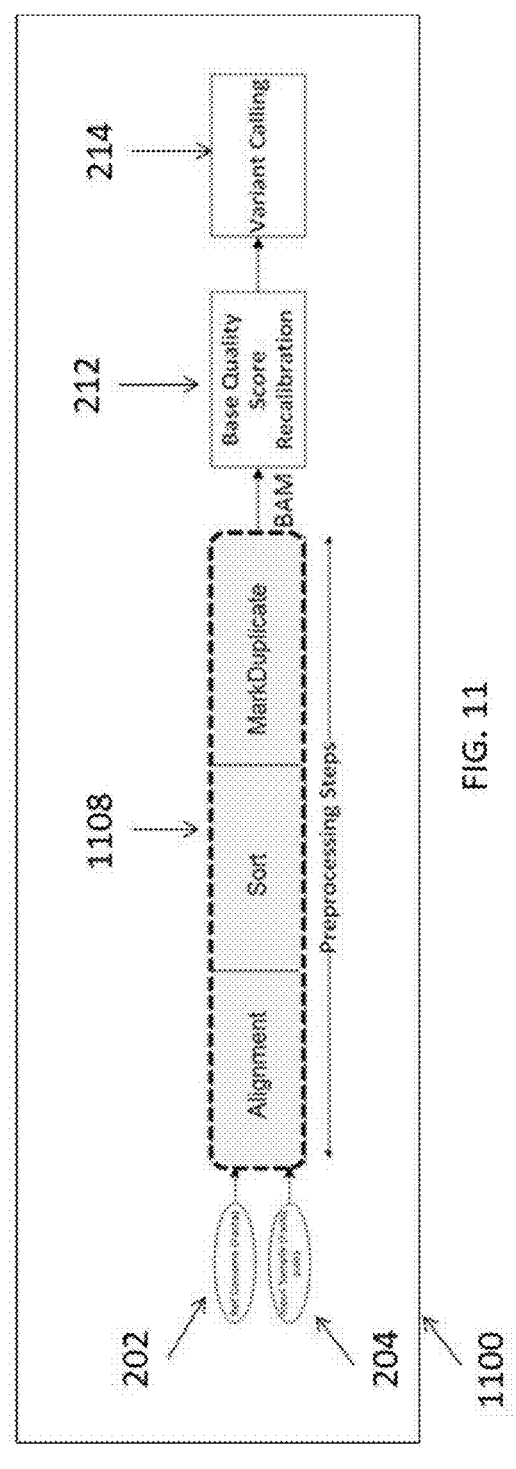

FIG. 11 shows a new sub-system 1108 which merges the MD operation performed by the MD sub-system 210 with the combined alignment and sorting operation performed by the MergeAlignSort sub-system 712, according to some embodiments. By merging the operations of the MD sub-system 210 with the MergeAlignSort sub-system 712, the BAM file write and read operations are eliminated. MD can be performed more efficiently. In FIG. 11, both the system 200 and a new gene sequencing system 1100 (hereinafter referred to as system 1100) that includes the new sub-system 1108 are shown, where the alignment operations, the sort operations, and MD operations are combined into one new operation performed by the new sub-system 1108 (hereinafter referred to as the MergeMD sub-system 1108).

Figure 12:
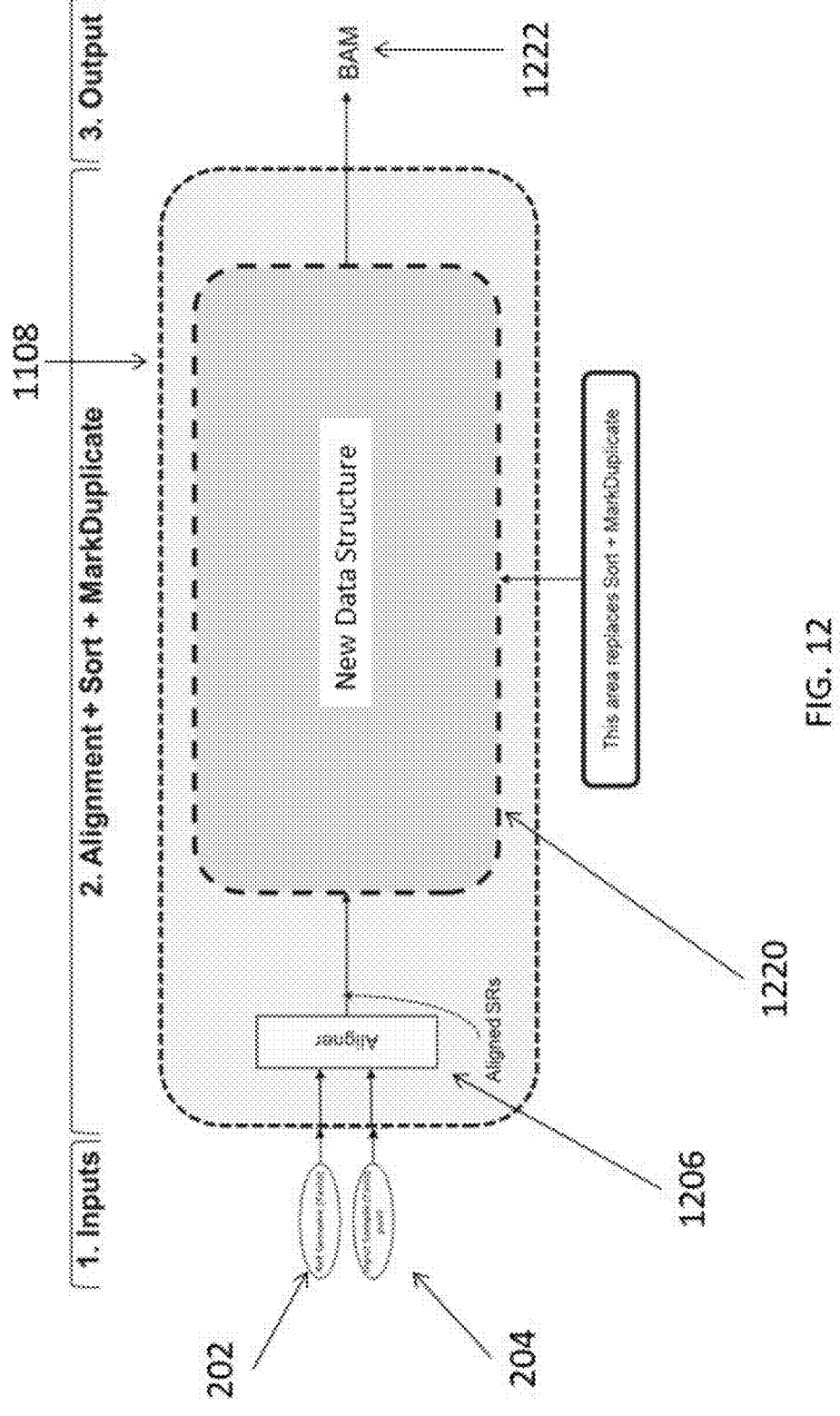
FIG. 12 shows a new sub-system of the second new gene sequencing system shown in FIG. 11, according to some embodiments.

FIG. 12 illustrates a block diagram of the new MergeMD sub-system 1108 according to some embodiments. The new MergeMD sub-system 1108 includes an aligner 106 and a new data structure 1220. The aligner 1206 receives the reference genome sequence 202 and the input genome sample sequence 204 as the input. After performing the MergeAlignSort operations as described above for each incoming aligned SR, the MD operations can be performed on the sorted SR. There is no need to write all the sorted SRs to an intermediate BAM file before start the MD operations as in the system 200. That is, after the position of one SR is found in the new data structure 1220, the corresponding SR metadata entry is used to perform the MD operations on the fly. The corresponding SR metadata entry can be used to find out whether the SR should be marked as duplicate or not. The output of the MergeMD sub-system 1108 may then be written to the BAM file for the next sub-systems (e.g., Base Quality Score sub-system 212) of the system 1100. The output BAM file 1222 contains the information about the SRs that are aligned, sorted, and with duplicate markings.

The MergeMD sub-system 1108 utilize the data structure 1200 which is similar to the data structure 620 with additional modifications. In some embodiments, two additional fields are added to the SR metadata entry described above. The first additional field in the SR metadata entry is a PNEXT field. This field keeps track of the distance between two mates' positions. As explained above, two SRs in a paired end are mates to each other. A maximum of 4 B may be used to keep track of the distance between two mates' positions.

The second additional field in the SR metadata entry is the average quality score (AQS), which is the average of quality scores (QSs) of all bps in an SR. In order to enable MD, the AQS for each SR is needed. The AQSs may be calculated in advance. In one example embodiment, the AQSs of the SRs may be calculated in the indexing step of the MergeAlignSort techniques as described above. By storing the AQS of the SR (2 Bytes), instead of storing the actual QSs of all bps in the SR (1 Bytes×the number of bps in the SR), additional memory space can be saved.

As described with respect to MergeAlignSort sub-system 712, an SR metadata entry is stored in the data structure 620 for each corresponding SR. The size of an SR metadata entry may be 14 Bytes. Here, to by adding extra 6 Bytes to each SR metadata entry (4 Bytes for PNEXT and 2 Bytes for the AQS), the required memory space for each SR metadata entry for MergeMD would be 20 Bytes (4B (ID)+10B (Flag, CIGAR, MD notation)+4B (PNEXT)+2B (AQS)). So, the total memory required for the data structure Boo for MergeMD may be 52.8 GB ((3.2 billion positions×4B per pointer per position)+(2 billion SRs×20 B per SR metadata entry)).

With the data structure 1220, in some embodiments, all SR metadata entries in a linked list (such as linked list 822) may be grouped and sorted based on their PNEXT values. SR metadata entries with the same PNEXT value are grouped together. The SR metadata entry with the highest AQS in each group may be at the beginning of each group and marked as not duplicate (e.g. MD0). The rest of the SR metadata entries in the same group are all marked as duplicate (e.g., MD1).

Figure 13:
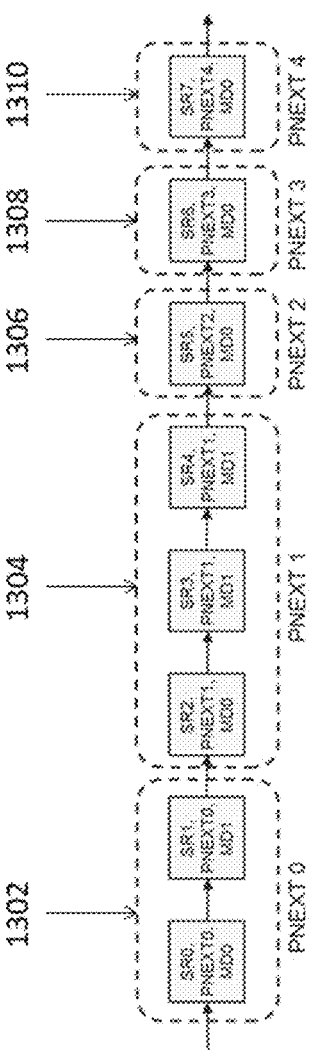
FIG. 13 illustrates an example linked list stored in the new memory data structure of the new sub-system of the second new gene sequencing system shown in FIG. 1i, according to some embodiments.

FIG. 13 illustrates an example linked list 1300 stored in data structure 1220 of MergeMD, according to some embodiments. Linked list 1300 contains 8 SR metadata entries: SR0 to SR7. The 8 metadata entries are sorted and grouped based on their PNEXT values. There are 5 groups in linked list 1300. SR0 and SR1 having the same PNEXT value (PNEXT0) are in the group 1302. That means, the respective mate SRs of SR0 and SR1 are at the same position of the reference genome. So, the distance between SR0 and its mate is the same as the distance between SR1 and its mate. Similarly, SR2, SR3, and SR4 having the same PNEXT value (PNEXT1) are in the group 1302. SR5 is the only SR metadata entry with the PNEXT2 value and is in the group 1306. SR6 is the only SR metadata entry with the PNEXT3 value and is in the group 1308. SR7 is the only SR metadata entry with the PNEXT4 value and is in the group 1310.

In some embodiments, the beginning entry of a group is the SR metadata entry with the highest AQS. For example, in the group 1302, SR0 has the highest AQS within the group and is marked with MD0 (not duplicate). SR1 in the group 1302 is marked with MD1 (duplicate). In the group 1304, SR2 has the highest AQS within the group and is marked with MD0 (not duplicate). SR3 and $SR_4$ in the group 1304 are marked as MD1 (duplicate). SR5, SR6, and SR7 are the only entry in their respective groups, so these three SR metadata entries are marked with MD0 (not duplicate).

If a new aligned SR comes in from the aligner 1206, and there is no SR metadata entry in the linked list at that alignment position, MergeMD may insert SR metadata entry, corresponding to the new aligned SR, in the linked list at that alignment position. The inserted insert SR metadata entry is marked with MD=0 because there is no duplicate at that position yet.

If there is already a linked list of SR metadata entries at the alignment position, such as the linked list 1300, sort and MD may occur at the same time. The sort part occurs after the new SR is aligned and the corresponding SR metadata entry is ready to be inserted in the linked list that is already sorted based on PNEXT values. The MergeMD sub-system 1108 may first traverse the linked list to find the insert position for the new SR based on the new SR's PNEXT value.

For the MD operation performed by the MergeMD sub-system 1108, if a group having the same PNEXT value as the new SR metadata entry's PNEXT value is found, the AQS of the beginning SR metadata entry of the group is compared to the AQS of the new SR metadata entry. If the new SR metadata entry has a higher AQS, MergeMD marks the beginning SR metadata entry (now with second highest AQS) with MD1 (duplicate), and marks the new SR metadata entry with MD0 (not duplicate), and inserts the new SR metadata entry at the beginning of the group in the linked list. That is, the new SR metadata entry becomes the new beginning SR of the group because it has the highest AQS of the group. If the new SR metadata entry has a lower AQS, MergeMD marks this new SR metadata entry with MD1 (duplicated), and MergeMD may insert the this new SR metadata entry just after the original beginning SR in that group in the linked list.

In FIG. 13, for example, if a new SR is aligned at the same position as the linked list 1300, a new SR metadata entry SR8 may be inserted in the linked list 1300. For the purpose of illustration, assume SR8 has the PNEXT1 value, the same as the entries in the group 1304. The AQS of SR8 is compared to the beginning SR of the group 1304, which is SR2. If the AQS of SR8 is higher than the AQS of SR2, SR8 is inserted right before SR2. SR8 is marked with MD0 (not duplicate), and SR2 is marked with MD1 (duplicate). On the other hand, if the AQS of SR8 is lower than the AQS of SR2, SR8 may be inserted right after SR2. SR8 is marked with MD1 (duplicate), and SR2 is still marked with MD0 (not duplicate).

So, utilizing the data structure 1220 with additional modifications allows the MD operations to be performed on the fly for each aligned SR (i.e., as each aligned SR comes without having to wait for all aligned SRs are generated). There is no need to have all SRs aligned or sorted before the MD operations start. Accordingly, there is no need to produce an unmarked intermediate BAM file between the sort operations and the MD operations. In essence, alignment, sort, and MD may be performed concurrently for each SR, which significantly reduces run time the MD operations and eliminates storage requirement to store intermediate files (e.g., the intermediate BAM files).

Figure 14:
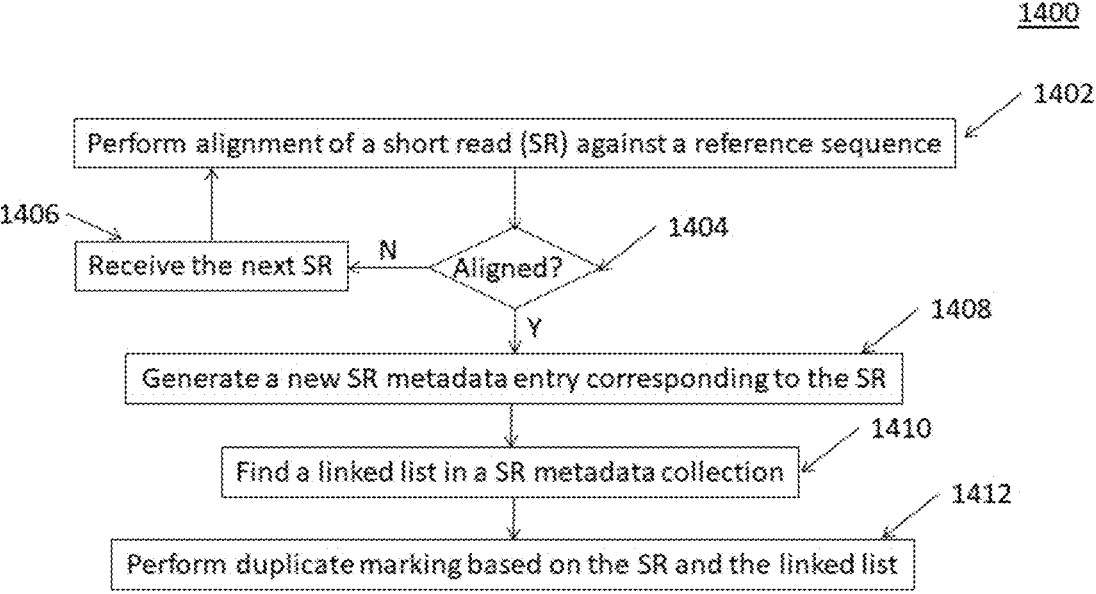
FIG. 14 shows a flowchart of a method performed by the new sub-system of the second new gene sequencing system shown in FIG. 1i, according to some embodiments.

FIG. 14 illustrates a flowchart of a method 1400 performed by the MergeMD sub-system 1108 for merging mark duplicate (MD) operations to the alignment and the sorting operations, according to some embodiments. The method 1400 may be carried out or performed by one or more processing units of a processing system, such as the PU 106 of the computing device 102, as described with respect to FIG. 1. Additional examples of the processing units may include, but are not limited to, central processing units (CPUs), graphics processing units (GPUs), tensor processing units (TPUs), application-specific integrated circuits (ASCIs), field-programmable gate arrays (FPGAs), artificial intelligence (AI) accelerators, or combinations thereof. The processing unit may include computer-readable code or instructions executing on one or more computing devices of a processing system, such as the computing device 102 of the processing system 100 as described with respect to FIG. 1. The method 1400 may be implemented by hardware, software, or a combination of hardware and software. Coding of the software for carrying out or performing the method 1400 is well within the scope of a person of ordinary skill in the art having regard to the present disclosure. The method 1400 may include additional or fewer operations than those shown and described and may be carried out or performed in a different order. Computer-readable code or instructions of the software executable by the one or more processing units may be stored on a non-transitory computer-readable medium, such as for example, the memory 108 of the computing device 102.

The method 1400 starts at the operation 1402, where the processing unit performs alignment of a short read (SR) against a reference sequence. The reference sequence comprises a first sequence of base pairs (bps). The SR comprises a second sequence of bps.

At the operation 1404, the processing unit determines whether the SR is aligned against the reference sequence. If the SR is not aligned, the processing unit receives the next SR at the operation 1406 and processes the next SR by repeating at the operation 1402. If the SR is aligned, in response to the determination that the SR is aligned with the reference sequence at a first position in the reference sequence, the processing unit generates a new SR metadata entry corresponding to the SR at the operation 1408.

At the operation 1410, the processing unit finds a linked list in a SR metadata collection. The first position of the linked list in the SR metadata collection corresponds to the first position of the reference sequence where the SR is aligned. At the operation 1412, the processing unit performs duplicate marking based on the SR and the linked list.

In some embodiments, the SR may be in a pair end comprising the SR and a mate SR. The new SR metadata entry may comprise an average quality score (AQS) of quality scores of the bps in the SR. The new SR metadata entry may further comprise a PNEXT value indicating a distance between the first position of the linked list in the SR metadata collection and a second position of a second linked list in the SR metadata collection. The second linked list may comprise a second SR metadata entry corresponding to the mate SR. In some embodiments, the SR metadata entries in the linked list may be grouped based on PNEXT values of the SR metadata entries in the linked list.

In some embodiments, to perform duplicate marking, the processing unit may find a group of SR metadata entries in the linked list having the same PNEXT value as the new SR metadata entry. The processing unit may then find a head SR metadata entry in the group, wherein an AQS of the head SR metadata entry is the highest in the group. Next, the processing unit may mark one of the new SR metadata entry or the head SR metadata entry as duplicate based on a comparison between the AQS of the head SR metadata entry and the AQS of the new SR metadata entry. In some embodiments, if the AQS of the new SR metadata entry is higher than the AQS of the head SR metadata entry, the processing unit may mark the head SR metadata entry as duplicate. If the AQS of the new SR metadata entry is lower than the AQS of the head SR metadata entry, the processing unit may mark the new SR metadata entry as duplicate.

In some embodiments, the head SR metadata entry may be at the beginning of the group in the linked list. The processing unit may insert the new SR metadata entry at the beginning of the group if the AQS of the new SR metadata entry is higher than the AQS of the head SR metadata entry. The processing unit may insert the new SR metadata entry after the head SR metadata entry if the AQS of the new SR metadata entry is less than the AQS of the head SR metadata entry.

In some embodiments, the processing unit may generate a binary alignment map (BAM) file based on the SR metadata collection without producing an intermediate (sequence alignment map) SAM file or an intermediate unmarked BAM file (i.e., a BAM file without duplicate marking). In some embodiments, the SR metadata collection may be an array of linked lists. The size of the array may be based on the size of the first sequence of bps in the reference sequence.

The disclosed system 1100 that includes the MergeMD sub-system 1108 provides significant technical improvement over the system 200. The SR metadata entry stores AQS instead of the actual QSs to reduce the memory requirements from (SR size) Bytes to 2 Bytes, which is a huge space saving. Unlike the MD sub-system 210, which waits for all SRs to be aligned and sorted before the MD sub-system 210 can start its global operations, the disclosed MergeMD sub-system 1108 may start the MD operations as soon as the first SR is aligned. The intermediate unmarked BAM file (300 to 500 GB) can be eliminated from the process. The MD operations are performed concurrently with the alignment and the sorting operations. As each new SR is received from the aligner 1206 and being placed in its corresponding memory positions (sort), the new SR is checked for duplicates based on the new SR's position and the AQS.

Figure 15:
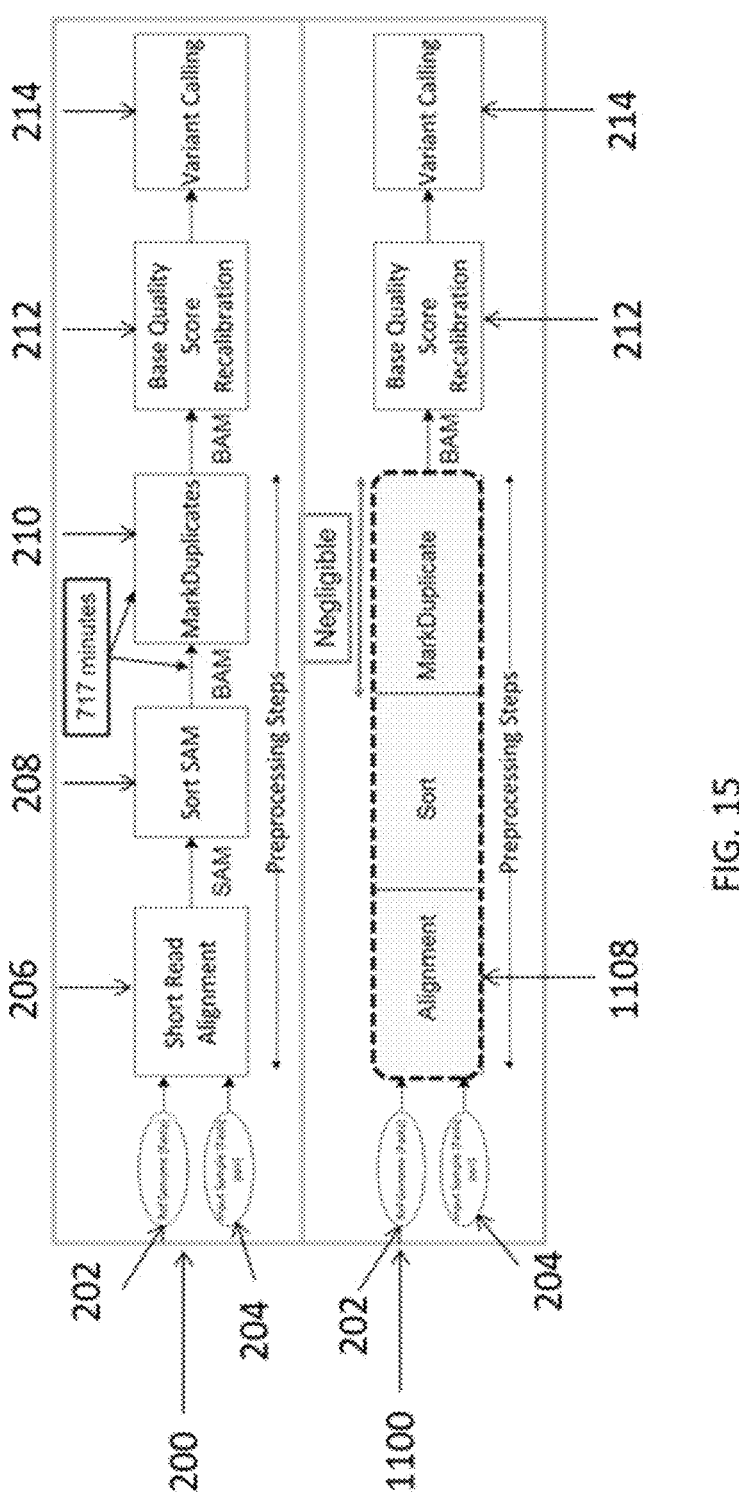
FIG. 15 illustrates some technical advantages of the second new gene sequencing system shown in FIG. 11.

FIG. 15 illustrates some technical advantages of the embodiment of the MergeMD sub-system 1108. Because there is no need for the intermediate BAM file write and read as the output of Sort, MD requires relatively very small processing time for locally detecting the duplicated SRs. In some testing environment for comparing the runtime of the system 200 with the runtime of the system 1110, the system 200 requires 717 minutes for the BAM file access and the MD sub-system. In contrast, the system 1100, marking duplicates can be performed much faster with an almost negligible amount of run time. The only remaining overhead would be the small local comparison of AQSs of the SR metadata entries for the same reference position, which, if performed in parallel, can take a negligible amount of time.

The disclosed embodiments also provide storage savings. Not having to write an intermediate BAM file as the output of the Sort SAM sub-system may result in a saving of 80-120 GB storage space. This is the result of in-memory processing of the operations performed by the MergeMD sub-system 1108. All preprocessing steps could be performed in memory, and there would be no storage I/O accesses.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

What is claimed is:

1. A method comprising:

performing, by at least one processing unit, alignment of a short read (SR) against a reference genome sequence, wherein the reference genome sequence comprises a first sequence of base pairs (bps), the reference genome sequence is at least a part of a full genome sequence, and the SR comprises a second sequence of bps;

determining, by the at least one processing unit, that the SR is aligned with the reference genome sequence at a first position in the reference genome sequence;

generating, by the at least one processing unit, a new SR metadata entry corresponding to the SR;

identifying, by the at least one processing unit, a linked list in a SR metadata collection, a first position of the linked list in the SR metadata collection corresponding to the first position of the reference genome sequence where the SR is aligned, wherein the SR is in a pair end comprising the SR and a mate SR of the SR, the new SR metadata entry comprises an average quality score (AQS) of quality scores of the bps in the SR, and the new SR metadata entry further comprises a distance indication value indicating a distance between the first position of the linked list in the SR metadata collection and a second position of a second linked list in the SR metadata collection, the second linked list comprising a second SR metadata entry corresponding to the mate SR;

performing, by the at least one processing unit, duplicate marking based on the SR and the linked list, wherein the performing the duplicate marking comprises:

identifying, by the at least one processing unit, a group of SR metadata entries in the linked list having a same distance indication value as the new SR metadata entry, identifying, by the at least one processing unit, a head SR metadata entry in the group, wherein an AQS of the head SR metadata entry is the highest in the group, and marking, by the at least one processing unit, one of the new SR metadata entry or the head SR metadata entry as duplicate based on a comparison between the AQS of the head SR metadata entry and the AQS of the new SR metadata entry;

inserting, by the at least one processing unit, the new SR metadata entry to the linked list such that SR metadata entries in the linked list are grouped based on distance indication values of the SR metadata entries in the linked list, the head SR metadata entry being positioned at a beginning of the group in the linked list, the inserting comprising:

inserting the new SR metadata entry at the beginning of the group as a new head SR metadata entry of the group if the AQS of the new SR metadata entry is higher than the AQS of the head SR metadata entry, or inserting the new SR metadata entry after the head SR metadata entry if the AQS of the new SR metadata entry is less than the AQS of the head SR metadata entry; and generating, by the at least one processing unit, a binary alignment map (BAM) file based on the SR metadata collection without producing an intermediate sequence alignment map (SAM) file and without producing an intermediate unmarked BAM file.

2. The method of claim 1, wherein the marking comprises:

if the AQS of the new SR metadata entry is higher than the AQS of the head SR metadata entry, marking, by the at least one processing unit, the head SR metadata entry as duplicate; and if the AQS of the new SR metadata entry is lower than the AQS of the head SR metadata entry, marking, by the at least one processing unit, the new SR metadata entry as duplicate.

3. The method of claim 1, wherein the SR metadata collection is an array of linked lists, and a size of the array is based on a size of the first sequence of bps in the reference genome sequence.

4. The method of claim 1, wherein the linked list includes a plurality of groups of SR metadata entries grouped based on distance indication values such that corresponding SR metadata entries in the linked list that have a same corresponding distance indication value are grouped together into a same corresponding group of the plurality of groups of SR metadata entries.

5. The method of claim 4, wherein only a corresponding current head SR metadata entry in each group of the plurality of groups of SR metadata entries is marked as non-duplicate.

6. The method of claim 1, further comprising:

performing, by the at least one processing unit, alignment of a second SR against the reference genome sequence concurrently with the performing the duplicate marking based on the SR.

7. A computing device comprising:

at least one processor unit;

a non-transitory computer readable storage medium storing programming for execution by the at least one processor unit, the programming including instructions to cause the computing device to perform operations including:

performing alignment of a short read (SR) against a reference genome sequence, wherein the reference genome sequence comprises a first sequence of base pairs (bps), the reference genome sequence is at least a part of a full genome sequence, and the SR comprises a second sequence of bps;

determining that the SR is aligned with the reference genome sequence at a first position in the reference genome sequence;

generating a new SR metadata entry corresponding to the SR;

identifying a linked list in a SR metadata collection, a first position of the linked list in the SR metadata collection corresponding to the first position of the reference genome sequence where the SR is aligned, wherein the SR is in a pair end comprising the SR and a mate SR of the SR, the new SR metadata entry comprises an average quality score (AQS) of quality scores of the bps in the SR, and the new SR metadata entry further comprises a distance indication value indicating a distance between the first position of the linked list in the SR metadata collection and a second position of a second linked list in the SR metadata collection, the second linked list comprising a second SR metadata entry corresponding to the mate SR;

performing duplicate marking based on the SR and the linked list, wherein the performing the duplicate marking comprises:

identifying a group of SR metadata entries in the linked list having a same distance indication value as the new SR metadata entry, identifying a head SR metadata entry in the group, wherein an AQS of the head SR metadata entry is the highest in the group, and marking one of the new SR metadata entry or the head SR metadata entry as duplicate based on a comparison between the AQS of the head SR metadata entry and the AQS of the new SR metadata entry;

inserting the new SR metadata entry to the linked list such that SR metadata entries in the linked list are grouped based on distance indication values of the SR metadata entries in the linked list, the head SR metadata entry being positioned at a beginning of the group in the linked list, the inserting comprising:

inserting the new SR metadata entry at the beginning of the group as a new head SR metadata entry of the group if the AQS of the new SR metadata entry is higher than the AQS of the head SR metadata entry, or inserting the new SR metadata entry after the head SR metadata entry if the AQS of the new SR metadata entry is less than the AQS of the head SR metadata entry; and generating a binary alignment map (BAM) file based on the SR metadata collection without producing an intermediate sequence alignment map (SAM) file and without producing an intermediate unmarked BAM file.

8. The computing device of claim 7, wherein the marking comprises:

if the AQS of the new SR metadata entry is higher than the AQS of the head SR metadata entry, marking the head SR metadata entry as duplicate; and if the AQS of the new SR metadata entry is lower than the AQS of the head SR metadata entry, marking the new SR metadata entry as duplicate.

9. The computing device of claim 7, wherein the SR metadata collection is an array of linked lists, and a size of the array is based on a size of the first sequence of bps in the reference genome sequence.

10. A non-transitory computer-readable medium having instructions stored thereon that, when executed by at least one processor unit, cause the at least one processor unit to perform operations, the operations comprising:

performing alignment of a short read (SR) against a reference genome sequence, wherein the reference genome sequence comprises a first sequence of base pairs (bps), the reference genome sequence is at least a part of a full genome sequence, and the SR comprises a second sequence of bps;

determining that the SR is aligned with the reference genome sequence at a first position in the reference genome sequence;

generating a new SR metadata entry corresponding to the SR;

identifying a linked list in a SR metadata collection, a first position of the linked list in the SR metadata collection corresponding to the first position of the reference genome sequence where the SR is aligned, wherein the SR is in a pair end comprising the SR and a mate SR of the SR, the new SR metadata entry comprises an average quality score (AQS) of quality scores of the bps in the SR, and the new SR metadata entry further comprises a distance indication value indicating a distance between the first position of the linked list in the SR metadata collection and a second position of a second linked list in the SR metadata collection, the second linked list comprising a second SR metadata entry corresponding to the mate SR;

performing duplicate marking based on the SR and the linked list, wherein the performing the duplicate marking comprises:

identifying a group of SR metadata entries in the linked list having a same distance indication value as the new SR metadata entry, identifying a head SR metadata entry in the group, wherein an AQS of the head SR metadata entry is the highest in the group, and marking one of the new SR metadata entry or the head SR metadata entry as duplicate based on a comparison between the AQS of the head SR metadata entry and the AQS of the new SR metadata entry;

inserting the new SR metadata entry to the linked list such that SR metadata entries in the linked list are grouped based on distance indication values of the SR metadata entries in the linked list, the head SR metadata entry being positioned at a beginning of the group in the linked list, the inserting comprising:

inserting the new SR metadata entry at the beginning of the group as a new head SR metadata entry of the group if the AQS of the new SR metadata entry is higher than the AQS of the head SR metadata entry, or inserting the new SR metadata entry after the head SR metadata entry if the AQS of the new SR metadata entry is less than the AQS of the head SR metadata entry; and generating a binary alignment map (BAM) file based on the SR metadata collection without producing an intermediate sequence alignment map (SAM) file and without producing an intermediate unmarked BAM file.

11. The non-transitory computer-readable medium of claim 10, wherein the marking comprises:

if the AQS of the new SR metadata entry is higher than the AQS of the head SR metadata entry, marking the head SR metadata entry as duplicate; and if the AQS of the new SR metadata entry is lower than the AQS of the head SR metadata entry, marking the new SR metadata entry as duplicate.

12. The non-transitory computer-readable medium of claim 10, wherein the SR metadata collection is an array of linked lists, and a size of the array is based on a size of the first sequence of bps in the reference genome sequence.

* * * * *